United States Patent
Källstrand

(10) Patent No.: US 10,575,752 B2
(45) Date of Patent: Mar. 3, 2020

(54) SYSTEM AND METHOD FOR DETERMINATION OF A BRAINSTEM RESPONSE STATE DEVELOPMENT

(75) Inventor: Johan Källstrand, Lund (SE)

(73) Assignee: SensoDetect AB, Lund (SE)

(*) Notice: Subject to any disclaimer, the term of this patent is extended or adjusted under 35 U.S.C. 154(b) by 774 days.

(21) Appl. No.: 13/820,470

(22) PCT Filed: Sep. 5, 2011

(86) PCT No.: PCT/EP2011/065340
§ 371 (c)(1),
(2), (4) Date: May 21, 2013

(87) PCT Pub. No.: WO2012/028749
PCT Pub. Date: Mar. 8, 2012

(65) Prior Publication Data
US 2013/0231581 A1 Sep. 5, 2013

Related U.S. Application Data

(60) Provisional application No. 61/379,748, filed on Sep. 3, 2010.

(30) Foreign Application Priority Data

Sep. 3, 2010 (EP) .................. 10175201

(51) Int. Cl.
*A61B 5/0484* (2006.01)
*A61B 5/00* (2006.01)
*A61B 5/12* (2006.01)

(52) U.S. Cl.
CPC ........ *A61B 5/04845* (2013.01); *A61B 5/4839* (2013.01); *A61B 5/12* (2013.01)

(58) Field of Classification Search
None
See application file for complete search history.

(56) References Cited

U.S. PATENT DOCUMENTS 5,287,859 A * 2/1994 John .............. A61B 5/0484
  600/544
6,493,576 B1   12/2002 Dankwart-Eder
  (Continued)

FOREIGN PATENT DOCUMENTS

JP     2011251058 A    12/2011
WO     WO2001060253 A1  8/2001
  (Continued)

OTHER PUBLICATIONS

European Patent Office, International Search Report, International Application No. PCT/EP2011/065340, dated Apr. 3, 2012, 5 pgs.
(Continued)

*Primary Examiner* — Etsub D Berhanu
(74) *Attorney, Agent, or Firm* — Inskeep IP Group, Inc.

(57) ABSTRACT

A system, method and computer program are disclosed that are adapted to detect a lateral brainstem response state development of a subject over a period of time as a function of a population of neurons evoked response patterns to sound stimuli. In these a sound stimuli generating unit is operative to repeatedly send a sound stimulus to the subject to evoke the neurons response patterns. The sound stimulus comprises a first and at least a second consecutive train of sounds pulses. A detection unit is operative to detect a brainstem response signal related to the neurons response patterns, wherein a first response signal is caused by the first train of sound pulses and a second response signal is caused by the second train of sound pulses. A storage unit may be included that is operative to store information based on the brainstem response signals. Further, a control unit is opera-
(Continued)

tive to determine the lateral brainstem response state development based on a comparison between the first and second response signals.

23 Claims, 15 Drawing Sheets

(56) References Cited

U.S. PATENT DOCUMENTS

| | | | |
|---|---|---|---|
| 6,556,861 B1 | 4/2003 | Prichep | |
| 6,743,183 B1 | 6/2004 | Thornton | |
| 2002/0099306 A1* | 7/2002 | Shaw | A61B 5/121 600/559 |
| 2003/0135128 A1* | 7/2003 | Suffin | A61B 5/0006 600/544 |
| 2004/0204659 A1* | 10/2004 | John | A61B 5/04845 600/559 |
| 2005/0203557 A1* | 9/2005 | Lesinski | A61B 17/1679 606/180 |
| 2007/0100251 A1 | 5/2007 | Prichep | |
| 2007/0299359 A1* | 12/2007 | Olsson | A61B 5/04845 600/544 |
| 2008/0125669 A1* | 5/2008 | Suffin | A61B 5/0006 600/544 |
| 2008/0167571 A1* | 7/2008 | Gevins | A61B 5/0484 600/544 |
| 2009/0312663 A1* | 12/2009 | John | A61B 5/0476 600/544 |
| 2010/0286549 A1* | 11/2010 | John | A61B 5/0476 600/544 |

FOREIGN PATENT DOCUMENTS

| | | |
|---|---|---|
| WO | WO2006062480 A1 | 6/2006 |
| WO | WO2006/122304 A1 | 11/2006 |
| WO | WO2006122304 A1 | 11/2006 |

OTHER PUBLICATIONS

European Patent Office, International Preliminary Report on Patentability, International Application No. PCT/EP2011/065340 dated Mar. 1, 2013, 22 pgs.

Hotz, M.A. et al. "Shifts in auditory brainstem response latencies following plasma-level-controlled aminoglycoside therapy", European Archives of Oto-Rhino-Laryngolgy, Springer International, Berlin, Germany, vol. 247, No. 4, Jun. 1, 1990, pp. 202-205.

Harkrider, Ashley Whicker et al., "Acute effect of nicotine on non-smokers", Hearing Research, Hearing Research, Elsevier Science Publishers, Amsterdam, NL, vol. 160, Jan. 1, 2001, pp. 73-88.

Japan Patent Office, Office Action dated Jul. 14, 2015 in Japanese Patent Application No. JP2013-526506, 5 pages.

* cited by examiner

SYSTEM AND METHOD FOR DETERMINATION OF A BRAINSTEM RESPONSE STATE DEVELOPMENT

RELATED APPLICATIONS

This application is the U.S. National Phase of and claims priority to International Patent Application No. PCT/EP2011/065340, International Filing Date Sep. 5, 2011, entitled System And Method For Determination Of A Brainstem Response State Development, which claims benefit of U.S. Provisional Application Ser. No. 61/379,748, filed Sep. 3, 2010 entitled System And Method For Determination Of A Brainstem Response State Development; and European Application No. 10175201.2, filed Sep. 3, 2010 entitled System And Method For Determination Of A Brainstem Response State Development; all of which are incorporated herein by reference in their entireties.

FIELD OF THE INVENTION

This invention pertains in general to the field of stimulatory, particularly auditory brainstem response, and related devices, systems and methods.

BACKGROUND OF THE INVENTION

It is known that auditory stimulation of a subject can be used to evoke brainstem response potentials but other stimuli than auditory may be used. Auditory brainstem response audiometry is a known screening test to monitor for hearing loss or deafness.

For instance international patent application WO 2008/006164 discloses a method for acquiring an auditory brainstem response, by presenting a plurality of stimuli, detecting electrophysiological signals in response to the stimuli, a recover signal is generated based on the stimuli and the response is determined from the electrophysiological signals and the recovery signal.

Recently new applications have evolved to diagnose certain brainstem disorders.

For instance, in international patent application WO 2006/062480, of the same applicant as the present application, which hereby is incorporated in its entirety for all purposes, a system and method is disclosed for diagnosis of brainstem disorders, such as schizophrenia.

WO2007/050780 discloses monitoring systems and methods for sensing biological and other responses reflecting various aspects of the nervous system associated with specific neurologic states. Stimulatory effects on a neurologic system are assessed. One method includes stimulating the neurologic system, monitoring at least one neurologic state for effects of the stimulation to the neurologic system, gathering multi-dimensional data from the monitoring of the at least one neurological state, and analyzing the multi-dimensional data to determine multi-dimensional interactions between the stimulation and the effects on the at least one neurological state. Neurologic states assessed comprise hypnotic, analgesia, relaxation, stress, depression, anxiety, allostasis, immune response, and combinations thereof. Neurological states may be affected by certain stimuli, including pharmaceutical stimuli. A method is disclosed in international patent application WO 2007/084979 for evaluating an effect of a psychotropic compound or a treatment on a neuronal activity of an animal including determining a change in the amount of information generated by neurons in response to at least one repeatedly applied stimulus. The change is caused by administering the psychotropic compound or a treatment. Also provided is a method of screening psychotropic compounds for effectiveness on an animal which involves using a change in sensory discrimination in a population of neurons of the animal, wherein the sensory discrimination is obtained in response to one or more stimuli repeatedly applied to the animal and wherein a change in the sensory discrimination occurs due to administering the psychotropic compounds to the animal.

U.S. Pat. No. 6,556,861 discloses A Fetal Brain Monitor (FBM) that utilizes a transducer which is placed on the abdomen of a mother and which is pulsed to generate auditory sounds, i.e., clicks, to provide auditory brainstem evoked responses (BAER) of a fetus within the mother's uterus. The fetus' brain waves are detected by a biosensor, amplified, converted to digital data, and analyzed, in one embodiment, using a digital comb filter to improve the signal/noise ratio. The computer system uses QEEG (Quantitative EEG) to compare the data from the fetus to normative data or to prior states of the fetus' own data (self-norm).

The basic idea disclosed in U.S. Pat. No. 6,556,861 is to compare the data to normative data from a population of fetuses to determine if the Brainstem Auditory Evoked Potentials are normal or abnormal. This is conducted by using unmodified clicks or pulses similar to those used for Brainstem Auditory Evoked Response monitoring. A briefly described alternative or complement to this could be to use a self-norm. The described self-norm refers to an initial recording being an initial state or a prior state of the fetus being monitored. Each successive recording being a session comprising an averaged multitude of stimuli is compared to a initial state (such as an identified start point) or prior state for determining a degree of change from the initial state. I.e. the fetal brain is assessed relative to an earlier state in the fetus to allow for a comparison of a successive measurement relative to some prior state. This is done to follow the development of the central nervous system of a fetus. The taught self-norm does not disclose repeatingly presenting to a subject a train of unmodified click within a short time span from and related to a train of modified clicks to solve the problem of having the measured data presented in absolute figures. Absolute figures is an issue and a non-desired entity when comparing for example the brainstem profile of one subject being under influence of a drug to another subject or to determine to which degree a subject responds to a certain substance. This is in particular of interest for determining the efficiency of a treatment, such as by medication taken for treating brain related diseases, like ADHD, depression, stress etc.

Moreover, the above referred prior art documents are very general. Variations between tested individuals are generally very high. The prior art disclosures do not take this into consideration. Variation is for instance caused by individually different cognitive abilities or awareness or medication effectiveness. This means that all tested subjects hitherto needed to be manually divided into groups of compatible individuals to avoid too large variations of test results. Moreover, the measurements recorded by the prior art rely on absolute values and not the effect of the tested individual. Furthermore, the stimuli applied are hard to clone or reproduce causing further variations in the recorded data. This makes it hard to perform reliable comparisons between measurements from one individual to another and by concentrating the measurements to small parts of the brain, complex patterns are missed out which could be used to see subtle variations, for example connected to pharmacology. Another drawback with the above described systems and methods are that the practitioner needs to know where to look for a certain anticipated effect since they do not cover responses from the whole brainstem.

Hence, an Improved technique for determination of brainstem response state development would be advantageous and In particular allowing for increased flexibility, cost-effectiveness, robustness, reliability and/or patient friendliness would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a system, a method, a computer-readable medium and a computer program, according to the appended patent claims.

A lateral brainstem response state development of a subject is determined over a period of time as a function of a population of neurons evoked response patterns to auditory stimuli. More particularly the invention provides obtaining a complex profile of a subjects lateral brainstem response state to auditory stimuli. Auditory stimuli are below referred to as "sound pulses", but can in some embodiments be transient peaks, clicks, tone bursts, or other suitable types of auditory stimuli suitable for repetitive presentation.

According to a first aspect of the disclosure, a device is provided that is adapted to detect a lateral brainstem response state development of a subject over a period of time as a function of a population of neurons' evoked response patterns to sound stimuli. The device comprises a sound stimuli generating unit operative to repeatedly send, over said period of time, an identical sound stimulus to said subject to evoke said neurons response patterns. The sound stimulus comprises a first train of unmodified sound pulses and at least one second consecutive train of modified sound pulses. Further, the device comprises a detection unit operative to detect a brainstem response signal related to said neurons' response patterns. A first brainstem response signal is caused by said first train of sound pulses. At least one second brainstem response signal is caused by said second train of modified sound pulses. Moreover, a storage unit is provided as operative to store information based on said brainstem response signals. Further, a control unit is operative to determine said lateral brainstem response state development, for each of said sound stimuli, based on a comparison of said first response signal and said at least one second response signal.

The same sound stimuli are presented to both the left and the right side of the subject, either simultaneously or alternatingly.

This is preferably done by a standardized sound source to the left and right auditory channel of the subject in order to provide repeatable, individual independent sound stimuli.

Thus lateral responses of the left and right brainstem respectively are detected.

Except from providing more data leading to a more accurate analysis it may for example be used to observe differences in the response between the left and the right side.

Alternatively, different sound stimuli could be presented to the left and the right side of the subject, either simultaneously or alternatingly.

The responses are measured no more than 10 ms after the offset of sound stimuli thus only neuronal responses from sub-cortical areas are recorded. The electrophysiological activity of sub-cortical structures is more robust and stable than activity recorded from cortical parts of the brain. The response patterns are presented in real-time to the user with an update time of activity of one second or faster. Measurement results are thus particularly advantageous by both being rapidly updated and highly stable.

Some effect of this is that differences in the obtained responses due to when a person starts to perceive an effect of e.g. a substance on the brain can be reliably detected with a very high time resolution. The effect may be of a psychoactive compound. In other embodiments the substance may comprise food. Alternatively or in addition, the substance may comprise medical drugs, chemicals, herbal compounds, gases, fragrances etc. The effect may thus be determined very early, even before the subject has become aware of the effect. Hence, the measurement is less distorted and contains less noise compared to if the test was carried out on the cortex, in part explained by the fact that the test subject is not yet aware of the sound stimuli and therefore has not had time to process it.

This is provided as responses are measured no more than 10 ms after stimulation. Measurements are suitably triggered, such as disclosed in international patent application WO 2006/062480, of the same applicant as the present application, which hereby is incorporated in its entirety for all purposes. This also makes it possible to carry out the test independently of the test subject's cognitive ability, alertness and medication.

Some embodiments of the inventive system provide for a generated first train of sound pulses being a train of predetermined and fixed sound pulses comprising at least one sound pulse that evokes at least one of the neurons in the brainstem. Upon the mentioned repetition of the sound stimulus, based on always identical sound pulses, the repetitive sound pulses evoke an averaged activity of a population of the subject's brainstem neurons. The generated second train of sound pulses comprises at least one modified sound pulse of the first train of sound pulses. This means the second train of sound pulses is different from the first train of sound pulses.

The modification of the first sound pulses, thus forming the second train of sound pulses, may be made by adding noise either before, after or on top of each sound pulse of the first train of sound pulses. Alternatively or in addition, the frequency of the first train of sound pulses may be increased or decreased. Alternatively or in addition, the amplitude of the first train of sound pulses may be changed to obtain the second train of sound pulses.

The second train of pulses may in some embodiments be at least one of the sound pulses of the first train of sound pulses in unmodified form. Hereby an exhaustion effect on the evoked the brainstem neurons may be tested.

One feature of the device is that even when focused to only evoke the response from at least one of the neurons the response signal will contain the information from all neurons of the brainstem. This is a lateral brainstem response.

In some embodiments the first response signal corresponds to the first train of sound pulses and provides a reference state signal that is obtained for the subject's lateral brainstem response state. Here, the control unit is operative to determine the lateral brainstem response state development based on a comparison between the second response signal and the reference state signal of the subject.

Since the test subject is his own reference the problems with absolute values are avoided for example when comparing one test subjects brainstem response state to that of another test subject-under influence of the identical substance.

In some embodiment a system is provided that is adapted to detect a lateral brainstem response state development of a subject comprising a device according to the aforementioned aspect The system is adapted to repeatedly generate and send, over a first period of time, a sound stimuli comprising a first train of sound pulses and at least a second consecutive trains of modified sound pulses to said subject.

In some embodiments the system is adapted to repeatedly generate and send sound stimuli comprising at least two consecutive trains of sound pulses to the subject, wherein the subject is not under influence of a psychotropic compound or substance or food or therapy. This is made to establish a lateral brainstem response state baseline of the subject to the second modified train of sound pulses.

The baseline is established to obtain the average brainstem activity of the test subject when not influenced, e.g. under influence of a psychotropic compound or substance or food. The development of the brainstem response states activity may then advantageously be calculated as a percentage from the baseline. This makes calculation less demanding despite the large amount of data provided by the measurement.

In some embodiments of the invention the system is adapted to repeatedly generate and send the sound stimuli to the subject wherein a subject's brainstem response state development is monitored and determined in real-time during a measurement session lasting a first period of time. The determination of the subjects brainstem response state development is then advantageously determined based on a comparison of a current lateral brainstem response state to the baseline of the subject.

Hence, in some embodiments the control unit is adapted to determine a short time effect or influence of a psychotropic compound or substance or food or a placebo on the subject's brainstem response state.

This may be advantageously used to monitor neurophysiological effects of psychotropic compounds or substance or food or therapy in real-time.

In some embodiments the system is adapted to repeatedly generate and send the sound stimuli to the subject during a first measurement session and then subsequently at least a second measurement session at a later occasion during a second period of time. The determination of the subjects brainstem response state development is then based on a comparison of the current lateral brainstem response state to the baseline of the subject. The baseline is established at the first measuring session, and is available for subsequent measurement sessions.

Hence, in some embodiments the control unit is adapted to determine a long term treatment effect or influence of a psychotropic compound or substance or food or a placebo on the subject's brainstem response state.

These long term related embodiments may be used to measure normalizations of deviations. This is due to the fact that the measured response states under a session are averaged and then compared to the baseline. This gives a user of the system or method the possibility to measure a psychotropic compound or substance or food clinical treatment effects over a longer period of time.

In some embodiments, different neurons responses to different sound stimuli are monitored simultaneously.

This may be used to show where and/or how a psychotropic compound or substance or food effects a test subject and may be an important tool for drug developers or research groups.

In some embodiments of the invention the detected lateral brainstem response state of a subject is basis for a psychoacoustic profile of a lateral brainstem response state of the subject.

This gives a psychoacoustic profile of a test subjects brainstem response pattern and since the test subject is his own reference it is possible to compare the profile with other subjects profiles.

In some embodiments the control unit is adapted to compare the profile to a profile from a database comprising a population of profiles, and, based on this comparison, to determine if the subject is under influence of a psychotropic compound or substance or food.

By using the profile of a subject and compare it to a profiles stored in a database system it is possible to detect what type of psychotropic compound or substance or food the subject is under influence of. The profile may also in a similar fashion be used to indicate what type of medication gives the best response of the subject and therefore helps the subject most. Hence, a therapeutic efficiency of substance may be determined by some embodiments.

In some embodiments the control unit is adapted to determine the psychotropic compound or substance or food quantitatively. In addition, or alternatively, the control unit is adapted to determine the psychotropic compound or substance or food qualitatively. All measurements and tests may be performed both quantitatively and/or qualitatively.

The system can, due to its robustness and low noise, detect small and subtle changes, differences or variations in influences effecting the subject, e.g. administered substances.

According to another aspect of the disclosure, a method is provided for detecting a lateral brainstem response state development of a subject over a period of time as a function of a population of neurons evoked response patterns to sound stimuli. The method comprises repeatedly presenting the subject with a sound stimulus, over the period of time, evoking the neurons response patterns wherein the sound stimulus comprising a first and at least a second consecutive train of modified sounds pulses. Further, the method comprises evoking a first response signal by the first train of sound pulses and evoking a second response signal by the second train of modified sound pulses. Moreover, the method comprises detecting a brainstem response signal related to the neurons response patterns. The method comprises determining the lateral brainstem response state development based on a comparison between the first and second response signals. The method further comprises: generating the first train of sound pulses comprising a train of predetermined and fixed sound pulses and upon repetition of the sound stimulus always identical sound pulses, and wherein the sound pulses determining an activity of the subject's brainstem neurons activity, and/or generating the second train of sound pulses comprising at least one modified sound pulse of the first train of sound pulses.

According to a further aspect of the disclosure, a computer-readable medium having embodied thereon a computer program for processing by a computer is provided. The computer may be a computing device, such as the control unit of the afore described device aspect of the disclosure for detecting a lateral brainstem response state development of a subject over a period of time as a function of a population of neurons evoked response patterns to sound stimuli, wherein the computer program comprising a plurality of code segments. A first code segment is provided for controlling a repeatedly presenting the subject with a sound stimulus evoking the neurons response patterns wherein the sound stimulus comprising a first train of sound pulses and at least a second consecutive train of modified sounds pulses, whereupon a first response signal is evoked by the first train of sound pulses and a second response signal is evoked by the second train of modified sound pulses. In a third code segment a brainstem response signal is detected from a measurement signal related to the neurons response patterns. In a fourth code segment the lateral brainstem response state development is detected based on a comparison between the first and second response signals.

Further embodiments of the invention are defined in the dependent claims, wherein features for the second and subsequent aspects of the invention are as for the first aspect mutatis mutandis.

Herein the term a "period of time" herein some times refers to as a measuring session or only session is defined as the period of time it takes either for performing a single measuring or a real-time monitoring or for establishing an effect of a psychoactive compound, substance, food or pharmaceutical drugs/medicament.

For a single measuring session the period of time may be shorter than 2 hours or preferably around 40 minutes. The period of time may be longer than 40 minutes. Preferably the time for a single session is in the time range of 20 minutes to 2 hours. In some cases the preferred period of time may be as short as a couple of minutes such as 1 to 10 minutes.

For real-time monitoring a period of time may be defined from a point in time before the compound or substance is administrated to the subject. The period of time for real-time monitoring might be stopped at a point in time where the effect of a compound or substance is active, stabilized or at a point in time where the effect starts to decline. The total period of time may in some embodiments comprise of at least two time periods, a first time period before administrating the compound or substance for establishing a baseline and at least a second time period which may be performed consecutively to the first time period, such as directly after administration of a compound or substance or within a time span of a couple of minutes to hours.

The first time period may shorter than 2 hours but preferably shorter than 40 minutes, such as about 20 minutes, such as about 15 minutes, such as about 10 minutes. The at least second time period may be shorter than 2 hours and preferably around 40 minutes. In some cases the first time period may be as short as a couple of minutes such as 1 to 10 minutes The second time period may for some embodiments depend on the period of time until the effect of the administrated compound or substance is activated, stabilized or starts to decline. The second time period may be shorter than 2 hours but preferably shorter than 40 minutes. The second time period may be longer than 40 minutes if the effect if a psychoactive compound, substance or food needs to be studied during a longer period of time. Preferably the period of time for a second time period is in the range of 20 minutes to 2 hours. In some cases the time period could be as short as a couple of minutes such as 1 to 10 minutes.

Alternatively and/or additionally, the second time period may in some real-time embodiments be subsequently performed having interruptions of days between each period of time.

Alternatively and or additionally, for detection, establishing or studying a long term treatment effect of for example psychoactive, chemical or herbal compounds, substances or foodstuff or fragrance more than one session or period of time may be used to detect a lateral brainstem response state development of a subject. The sessions (such as first, second third session and so on) or periods of times may in these cases be subsequently performed. Between two subsequent sessions a particular time will laps such as hours, days, weeks or months. In most cases the particular time between two sessions is substantially longer than a single session or time period. The subsequently performed sessions may herein be referred to as a first period of time or a first session and the subsequently performed time periods may be referred to as at least a second period of time or at least a second session, such as a third period of time, such as a fourth period of time, such as a fifth period of time and so on. Usually, all subsequently performed sessions take place over a time period of weeks but may also be months or years.

Auditory stimuli may be defined or referred to as "sound pulses" or signals, including but not limited to, transient peaks, clicks, tone bursts, or other suitable types of auditory stimuli suitable for repetitive presentation. The stimuli should be auditory perceptive to the subject to whom the stimuli is presented. Thus as defined within the area of psychoacoustics the sound stimuli presented to a human subject may have any frequencies between 20 Hz and 20000 Hz, and the amplitude may be from the lower limit of audibility defined as 0 dB or higher but preferably below damaging level for the frequencies used. Preferably may be to use an amplitude being a minimum threshold amplitude or higher for the particular frequencies used, but below damaging level for the frequencies. Preferably the amplitude may be between about 0 to 120 dB, preferably between about 0 to 100 dB, preferably between about 0 to 90 dB, preferably about 70 dB.

The time width or duration of each sound pulse may be in the range of 0.1 to 1000 ms. Preferably the time with or duration of each sound pulse may be approximately the time of the detection of the evoked response of the brainstem, thus preferably between 0 to 100 ms, such as 0 to 50 ms.

Consecutive second trains follow immediately after first trains within a sound stimuli. Even "following immediately" after each other, a certain time gap may exist in practice at the transition segment between consecutive second trains that follow after first trains within a sound stimuli. Such a time gap between these trigged recordings is in embodiments approximately in the range of 1 ms to 10000 ms, preferably at least about 50 ms—in order for the recordings to not be affected by temporal integration. Similar gaps may be found between sound pulses within a single train. The detectable lateral brainstem response state development may be used to detect the effect pharmaceutical drugs/medicament may have on a subject for treatment, ease or relive of a disorder and/or disease. Wherein the subject could suffer from for example brainstem disorders; disorders of the nervous system or on neural states or other form of diseases or disorders having detectable lateral brainstem response states. Examples, but not limited to, may be drugs related to: ADHD, depression, anxiety, bipolar disorder, schizophrenia, Asperger syndrome, epilepsy, stress, relaxation, pain, immune response, allostasis; hypnotic, analgesia or similar.

A psychoactive, chemical or herbal compound or substances may refer to different types of drugs such as medical drugs, psychoactive drugs, psychopharmaceutical, psychotropic, anesthesia, pain controllers, psychiatric medication, illicit drugs, drugs of abuse and drugs associated thereof. Compound or substances may refer to compound or substances have an influence on a subject or patient's central nervous system or may affect the brain functioning resulting in changes in perception, mood, consciousness, cognition or behavior.

Therapy may herein refer using a drug or counseling, such as different kind of psychotherapy, for to treatment of a diagnosis or ease of symptoms but may also refer to drug or counseling for preventive therapy or supportive therapy.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
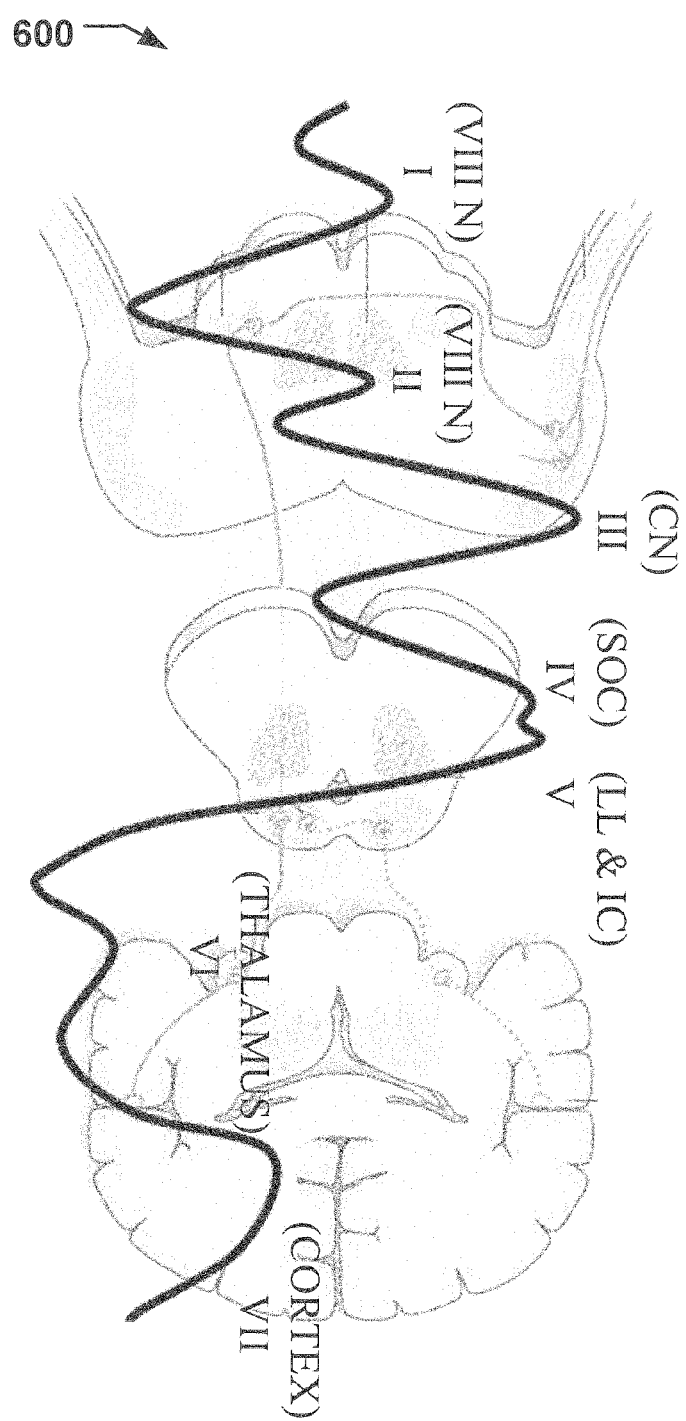
FIG. 1 is a graph that illustrates a typical brainstem response audiogram.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 is a graph 600 that illustrates a typical brainstem response audiogram. There are about thirteen different sound pulses known to evoke a brainstem response. In WO 2006/062480, of the same applicant as the present application which is incorporated by reference herein in its entirety for all purposes, such sound pulses are described in detail.

Figure 2:
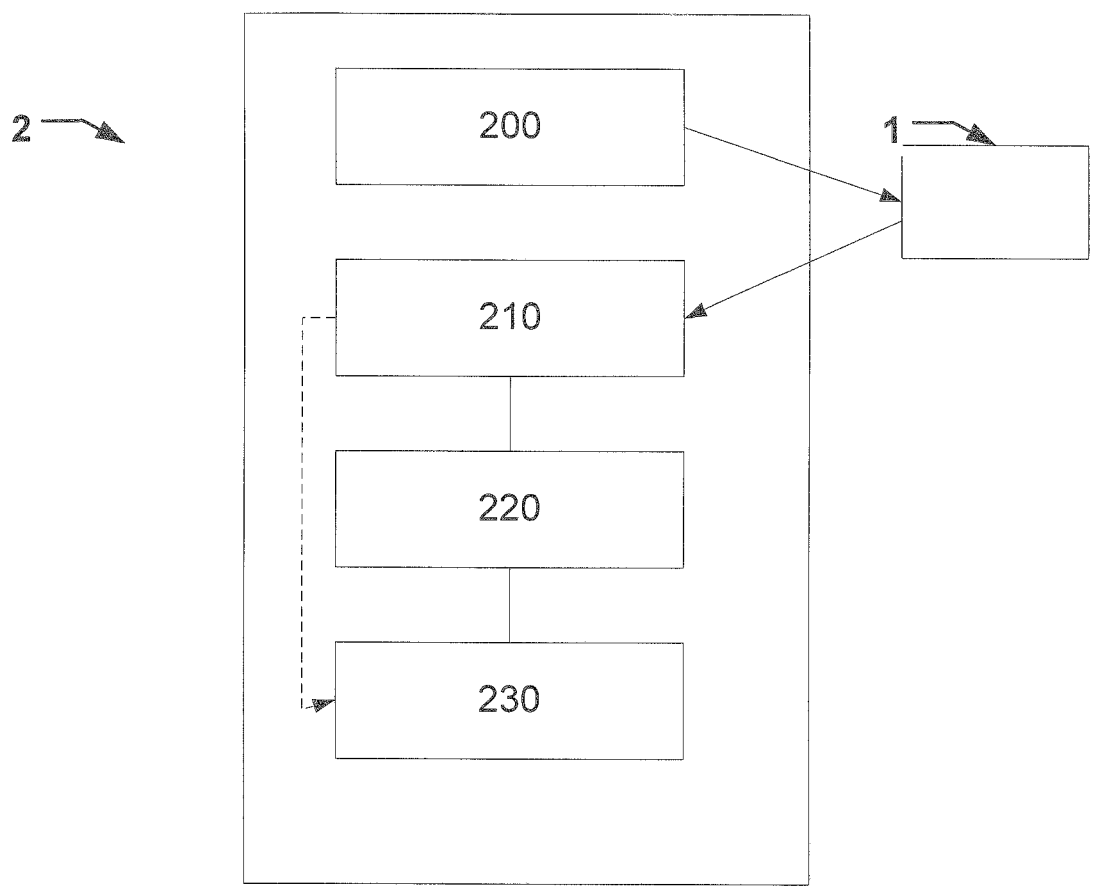
FIG. 2 is a schematic diagram of a device 2.

In an embodiment a device 2 is now described, which is illustrated with reference to FIG. 2. A sound stimuli generating unit 200 is operative to repeatedly generate and send a sound stimulus to a subject 1, wherein the generated sound stimuli is known to evoke neurons response patterns related to the brainstem. The generated stimulus comprises at least two consecutive trains of sound pulses. The first train of sound pulses comprises at least one sound pulse known to evoke a response from at least one neuron of the brainstem. The second train of sound pulses comprises at least one modified sound pulse of the first train of sound pulses.

Alternatively and/or additionally, the first train may comprise more than one similar sound pulse, such as a plurality of identical sound pulses, such as about 2 to 1000 or more, such as about 2 to 500 or more, such as about 2 to 100, such as about 2 to 50, such as about 2 to 10.

Alternatively and/or additionally, the first train may comprise more than one type of sound pulse.

The sound pulses of the first train are all known to evoke the brainstem response from different neurons.

In some embodiments the sound pulses used in the first train of the generated sound stimuli is at least one of the about 13 sounds known to evoke a brainstem response.

Alternatively and/or additionally, in some embodiments all 13 sounds known to evoke a brainstem response are used in the first train of sound pulses. The sound pulses used in the first train of sound pulses are complex and broad banded.

After the subject 1 has been presented with a first train of sound pulses a consecutive second train of sound pulses is generated and presented to the subject 1. Thus a first train of sound pulses is directly followed by at least a second train of sound pulses.

Alternatively and/or additionally, in some embodiments there may be a gap between the first train of pulses and the consecutive second train of pulses being directly following the first train of sound pulses.

The second train of sound pulses may comprises at least one of the sound pulses present in the first train of sound pulses but in a modified form.

Alternatively and/or additionally, the second train may comprise modified versions of at least one of the sound pulses present in the first train of sound pulses.

Alternatively and/or additionally, the second train may comprise modified versions of all of the sound pulses used in the first train of sound pulses.

The second train of sound pulses may comprise of the chosen sound pulses from the first train of sound pulses modified and/or modulated by being masked with a noise. The noise can either be added before or after or on-top of each sound pulse of the second train. Thus registering a response provides a measure of the impact of the added noise to the sound signals on the subject 1.

Alternatively or in addition to adding noise, certain frequencies may be extracted from each sound pulse and thus testing the impact of high/low frequencies on the subject 1.

Alternatively or in addition, other modifications, in any combinations, may be to change the amplitude of the sound pulses to register the different responses of the subject 1.

Alternatively or in addition, other modifications and/or modulations, in any combinations, may be to change the rise and fall time of the sound pulses.

An alternative to modify the sound pulses of the second train may be to repeat a large number of times one or more of the same sounds of the first train of sound pulses to register the exhaustion effect of the neuron of the brainstem of the subject 1.

Additionally and/or alternatively, the exhaustion effect may be obtained by using a second train comprising a large number of similar modified sound pulses.

In one embodiment of the invention the first train of sound pulses may be followed by two or more consecutive trains of modified sound pulses.

Sound stimuli may be presented to both the left and the right side of the subject 1 to obtain a complete lateral brainstem response state of the subject 1 either simultaneously or alternatingly.

Alternatively and/or additionally the same sound stimuli is used for both the right and the left ear.

Alternatively and/or additionally different sound stimuli is used for the right and the left ear.

A train of sound pulses may comprise a number of pulses, such as 1 to 1000 consecutive pulses, being presented to the subject 1.

A detection unit 210 detects a brainstem response signal related to the evoked neurons response patterns, wherein a first response signal is caused by a first train of sound pulses and a second response signal is caused by a second train of sound pulses.

Optionally a storage unit 220 may be used to store the data for later use.

A control unit 230 is provided for analyzing and determining the lateral brainstem response state development of a subject 1. During the repeatedly generating and sending of at least two consecutive trains of sound pulses the response signals related to each train of sound pulses are obtained and recoded. The response signals obtained may be the responses from all neurons and not only from the neurons selected to be evoked by the choice of sound stimuli. Hence a more complex and complete data-set is provided which may be used to improve the analysis.

Alternatively and/or additionally, in some embodiments the first and second train of sound pulses may comprise one sound pulse the response signal related to the train of sound pulses may be the response signals obtained from the single sound pulse of the train of sound pulses.

Alternatively and/or additionally, in some embodiments the first and the second train of sound pulses may comprise more than one sound pulse the response signal related to the train of sound pulses may be an average of the response signals obtained from each sound pulse of the train of sound pulses.

When for each repeatedly generated and sent sound stimuli, the response signals related to a first train of unmodified sound pulses is compared to response signals related to at least a second train of modified sound pulses, whereby each subject becomes its own reference. Hence giving a much more accurate and stable result compared to only obtaining and/or using absolute values. The self-reference is providing relative values of effects which may be caused by changes in the stimulating sound pulses. This may be by utilizing specific modifications on a second train of sound pulses in a repeated sound stimuli presented to a subject and subject's evoked brainstem response thereof. These effects may be established more stably than by using a repeated single sound pulse or modified sound pulse. Thus, these relative values may, for example, be able to show an effect of a psychoactive compound or substance on a subject. Therefore, by using the test subject as his own reference, when conducting the measurements, variance within subjects from measurement to measurement and variance between different subjects may be avoided. Thus, these provided relative values provide an independent measure rather than giving a confounding measure as would be the case when using absolute vales. These variances between subjects and within a subject, as previously mentioned, may be quite high when obtaining absolute values; hence much more stable results of an effect may be established compared to using absolute values.

The self-reference is making it possible to compare different individuals even when they are not part of the same defined group, thus test subjects with different cognitive abilities, awareness and medication may still be compared. Thus, there is no requirement of putting subjects into compatible groups. Further, variations in the recorded data, which may be caused by instabilities in the generated sound stimuli and in the recording of the responses, may be avoided by the same principals.

By the above, a psychoacoustic profile of a subject generates a complex response pattern. As an achievement of using the relative measure of the self-reference, the recorded pattern varies substantially between different subjects as a result of the effects in the brainstem response due to changes in the stimulating sound pulses. When utilizing the presented invention, the generated response pattern does not comprise absolute measurement values, but is based on the individual subjects brainstem's perceived characteristic of one sound pulse's effect on another sound pulse, see FIG. 8a-c. This effect one sound pulse has on another may be expressed in a change in percent. Inventors suppose that this surprising effect is anatomically and physiologically based on the electrical activity in one or more neurons or groups thereof may be affected by a change in the acoustic parameters of the acoustic stimuli (frequency, amplitude, etc.), as well as this processing is present in both sides of the brain. Thus an obtained complex pattern may be a platform for finding small, or even tiny, differences caused by the substances influencing a subject. Such small changes may neither be detected by means of any conventional auditory stimulation, nor without a system adapted for the psychoacoustical functioning of the central nervous system.

In some embodiments of the invention, a baseline is first determined for an individual subject. This obtained baseline is a reference value for the individual subject. As measurement values are affected in the short-term and/or long-term in different ways relative the baseline by different substances or compound and/or different dosages of a substance or compound influencing the subject, a robust, reliable measure of the effect is provided. As the subject is his own reference and there is no need for absolute measurement values, and all drawbacks related to absolute measurement values are avoided. Changes are analyzed of the electrophysiological activity in the brain stem based on psychoacoustic stimulation for a specific subject in relation to defined substances influence on the subject. Substances may include pharmaceutical compounds, chemical substances, foodstuff, naturopathic preparations, gases, scents, etc.

The measurements and analysis are in particular suitable for easy reproducibility, and do not need a complex technical system for handling and/or analysis. A battery of sound trains can be cloned for reproducibility. A standardized sound source contributes further to reproducibility of measurement results.

Measured short-term effects and changes in relation to the baseline, provide for pharmacokinetic determination of the effect of pharmaceutical substances on the subject.

Alternatively, or in addition, measured long-term effects and changes in relation to the baseline, provide or are used for determination of the effectiveness of a therapeutic treatment with pharmaceutical substances of the subject.

Additionally and/or alternatively, the short and/or long term effects may be determined in real-time during at least one measuring session.

Pharmaceutical research or clinical trials may thus be facilitated.

A placebo intake may be reliably detected by an absence of a difference to the determined baseline of a subject.

Additionally and/or alternatively, a baseline may be established over a number of subsequently performed sessions.

Adjustment of an optimal therapeutic treatment of a subject may thus be facilitated.

Alternatively, or in addition a topographic determination and comparison of where a substance taken by the subjects affects the brainstem may be made.

The aforementioned complex response pattern may provide a profile which may be used for qualitative and/or quantitative determination of substances taken by a subject.

The control unit 230 may be operative to provide the above and below mentioned functions, such as comparisons, determination of values, control of measurement, control of stimuli, etc.

The control unit 230 may comprise a computing unit for executing software code segments. Examples are given below.

Figure 3:
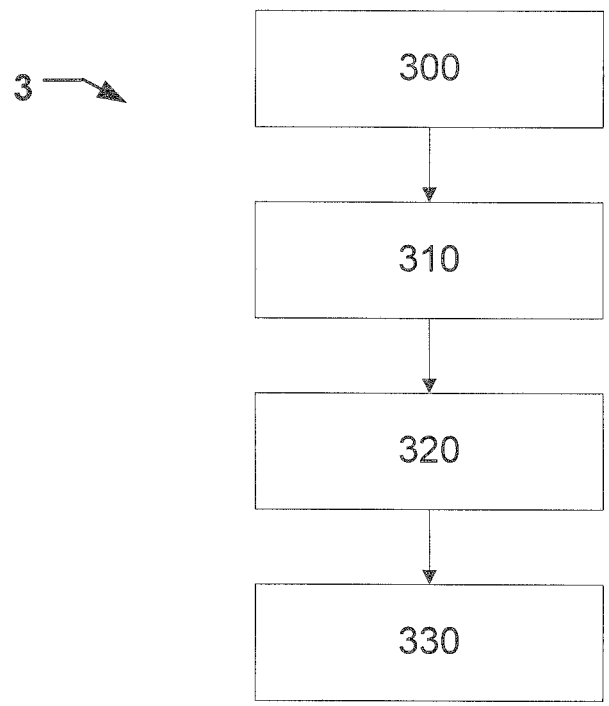
FIG. 3 is a flow chart that illustrates a method 3.

In FIG. 3, a flow-chart is used to illustrate a method 3 for detecting a lateral brainstem response state development of a subject over a period of time as a function of a population of neurons evoked response patterns to sound stimuli. The method starts with repeatedly presenting 300 a subject with sound stimuli evoking the subject brainstem neurons. The stimulus comprises a first and at least a second train of sound pulses. The sound stimuli evokes corresponding a first and at least a second response signals 310 relating to the first and the second train of sound pulses respectively. These response signals will be detected 320 and analyzed to determining 330 lateral brainstem response state developments based on comparing at least the first and the second response signal.

The described device and method may result in data with low noise which is characterizing the invention and makes it possible to see and catch small and subtle variations in the recorded response signal. The low noise is due to the vast amount of recorded data. This vast amount of data makes it possible to use analyzing methods to filtering out randomness in the data, corrupt data and noise. Further the low noise is also due to the fact that all of the recorded data come from evoked response signals related to neurons that are part of the sub-cortical part of the brain. The sub-cortical structures are also more robust than other part of the brain making the results stable, robust and reliable compare to other neurophysiological techniques like EEG.

For example the important feature that a tested subject being its own reference would not be as beneficial employing cortical EEG-techniques due to variations in the measured data. These variations in EEG-techniques may be caused by the complexity of the numbers of electrodes used and noise added to the response signal due to the distance of an occurrence of response in the brain from the source. Such methods might therefore neither be robust nor stable enough to detect small changes in the brain. The measured data using the invented device and method is little affected by the tested subjects cognitive ability, alertness and medication.

All of the proceeding embodiments rely on and may be carried out due to the low noise of the data mentioned above.

Figure 4A:
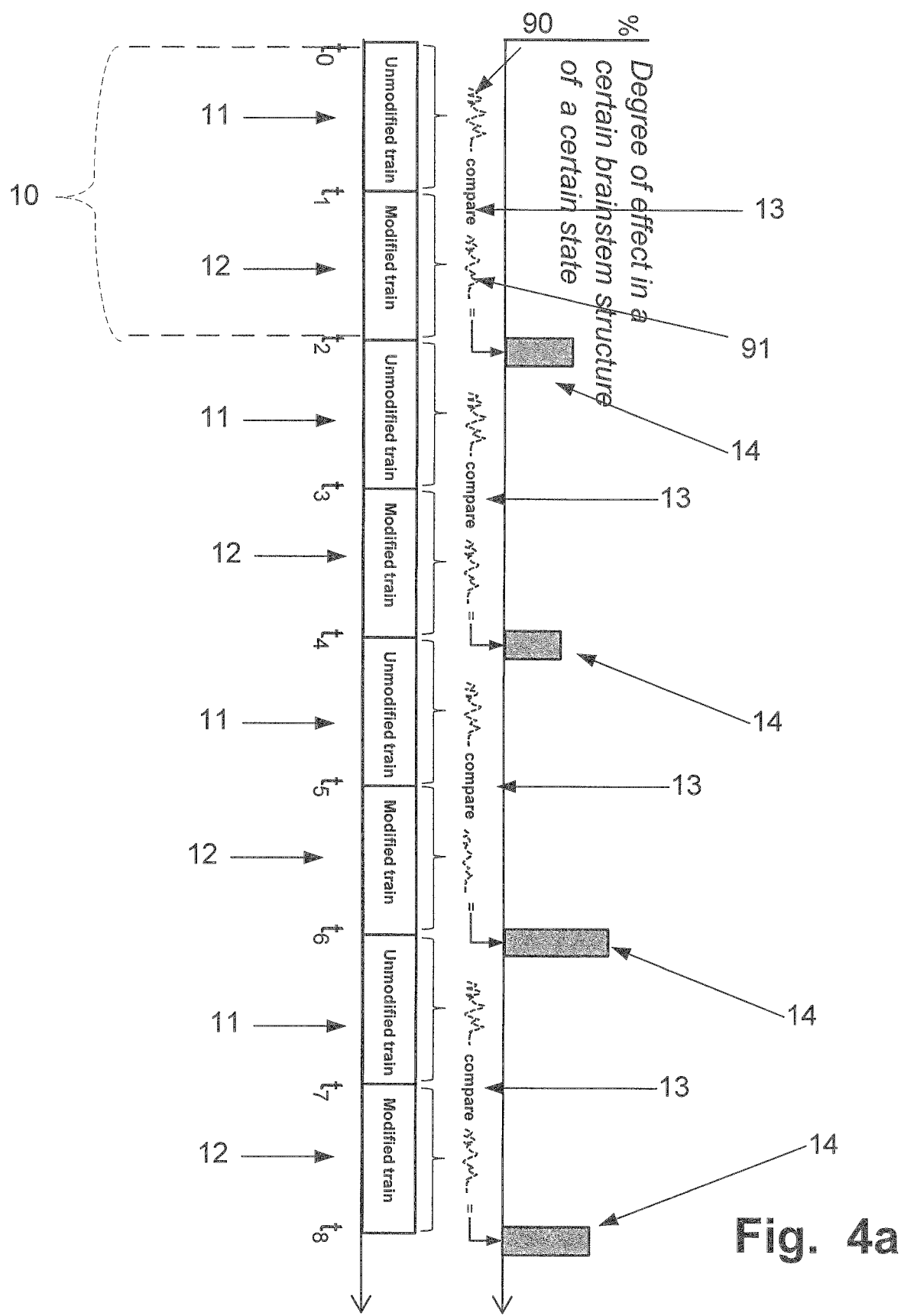
FIG. 4a is for an illustrative purpose showing repeatedly generated sound stimuli wherein in each sound stimuli comprises of a train of unmodified sound pulses with a consecutive train of modified sound pulses.

FIG. 4a is illustrating an exemplary embodiment of the invention wherein a generated sound stimuli 10 comprises two trains of sound pulses, a first train of unmodified sound pulses 11 and a consecutive second train of modified sound pulses 12. The first and second train of sound pulses 11, 12 may comprise either one or a plurality of sound pulses, such as a battery of sound pulses. At to a train of unmodified sound pulses 11 is generated and sent to the subject. For each unmodified sound pulse of the first train of sound pulses 11 generated and sent to the subject, a response signal from the evoked brainstem of the subject is obtained by using a trigged recording. Should the first train of sound pulses 11 comprise of more than one unmodified sound pulses an average will be made of the recorded response signals. The established response signal or averaged response signal corresponding to the first train of unmodified sound pulses 11 at $t_1$ is called the first response signal 90.

At $t_1$ a second train of modified sound pulses 12 is generated and sent to the subject. For each modified sound pulse of the second train of sound pulses 12 generated and sent to the subject, a response signal from the evoked brainstem of the subject is obtained using a trigged recording. Should the second train of modified sound pulses 12 comprise of more than one modified sound pulses an average will be made of the recorded response signals. The established response signal or averaged response signal corresponding to the second train of modified 12 sound pulses at $t_2$ is called the second response signal 91.

At t2 the first response signal 90 corresponding to the first train of unmodified sound pulses 11 is compared 13 to the second response signal 91 corresponding to the second train of modified sound pulses 12. This will provide in percentage, a degree of effect in a certain brainstem structure of a certain state 14 at time t2. The whole procedure is then repeated n-times over a certain period of time.

Hence, the measured variable is presented as a modified train evoked brainstem response 91 as a percentage of unmodified evoked response 90. In those cases the first and at least a second response signals are averaged, the measured variable is presented as a modified train averaged evoked brainstem response 91 as a percentage of the unmodified average evoked response 90.

Figure 4B:
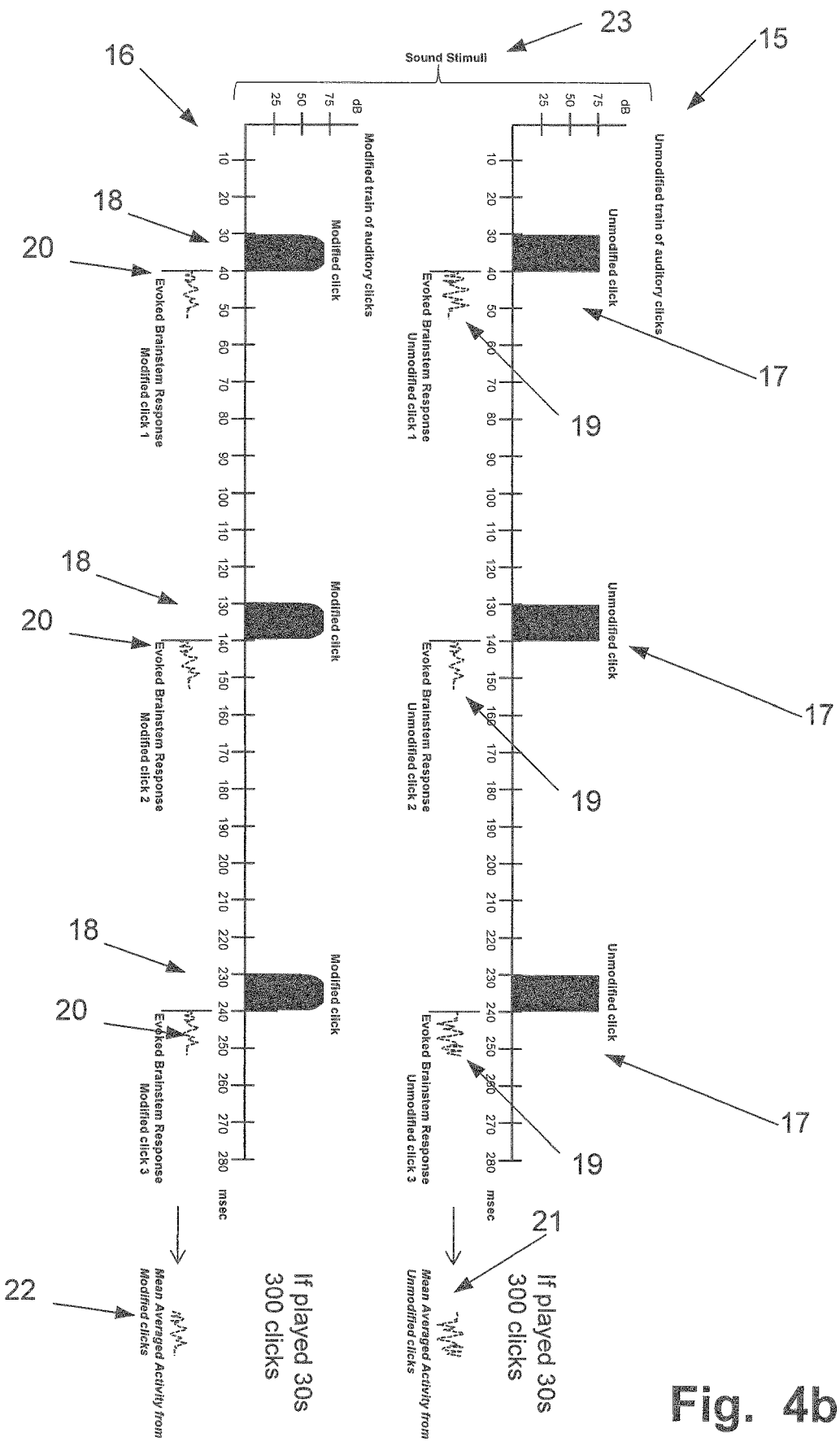
FIG. 4b is for an illustrative purpose showing a generated sound stimuli comprising of two trains having an arbitrary number of sound pulses and wherein the second train is modified by having a lower amplitude and rise and fall time.

FIG. 4b illustrates an example of sound stimuli 23 that may be used according to some embodiments of the invention. The sound stimuli 23 comprises of two trains of sound pulses, the upper is a first unmodified train of sound pulses 15 and the lower is a second train of modified sound pulses 16. Each unmodified sound pulse 17 is in this example an unmodified square shaped click having a 10 ms duration. The modified sound pulse 18 is a modification of the unmodified click having lower amplitude and rise and fall time. Each unmodified or modified sound pulse will give rise to an evoked brainstem response 19, 20.

With reference to FIG. 4a, each block illustrating a first train of unmodified sound pulses 11 may comprise a singles unmodified sound pulse 17 as of the upper part 15 of FIG. 4b. In this example, after the single unmodified sound pulse 17 of the first train of sound pulses 15 is presented to the subject, a trigged recording of the evoked brainstem response 19 will be obtained, i.e. a first response signal.

Alternatively, each block in FIG. 4a illustrating a first train of unmodified sound pulse 11 may comprise a plurality of unmodified sound pulse 17 as of the upper part 15 of FIG. 4b, such as 1 to 1000 unmodified sound pulses 17, such as 3, such as 10, such as 50, such as 500.

In the example given in FIG. 4b a first train of unmodified sound pulses 15 may comprise of 300 sound pulses 17 which will take about 30 sec to send to a subject and record trigged evoked brainstem responses corresponding to each of the 300 unmodified sound pulses 17. Thereafter a mean average activity 21 is calculated from the, in this example, 300 evoked brainstem response signals 19 corresponding to each unmodified sound pulse 17 of the first train of unmodified sound pulses 15, i.e. the mean average activity 21 may be a first response signal.

With reference to FIG. 4a, each block illustrating a second train of modified sound pulses 12 may comprise a singles modified sound pulse 18 as of the lower part 16 of FIG. 4b. In this example, after the single modified sound pulse 18 of the second train of sound pulses 16 is presented to the subject, a trigged recording of the evoked brainstem response 20 will be obtained, i.e. a first response signal.

Alternatively, each block in FIG. 4a illustrating a second train of modified sound pulses 12 may comprise a plurality of modified sound pulses 18 as of the lower part 16 of FIG. 4b, such as 1 to 1000 modified sound pulses 18, such as 3, such as 10, such as 50, such as 500. In the example given in FIG. 4b a second train of modified sound pulses 16 may comprise of 300 modified sound pulses 18 which will take about 30 sec to send to the subject and record trigged evoked brainstem responses 20 corresponding to each of the 300 modified sound pulse 18. Thereafter a mean average activity 22 is calculated from the, in this example, 300 evoked brainstem response signals 20 corresponding to each modified sound pulse 18 of the second train of modified sound pulses 16, i.e. the mean average activity 22 may be a second response signal.

Figure 4C:
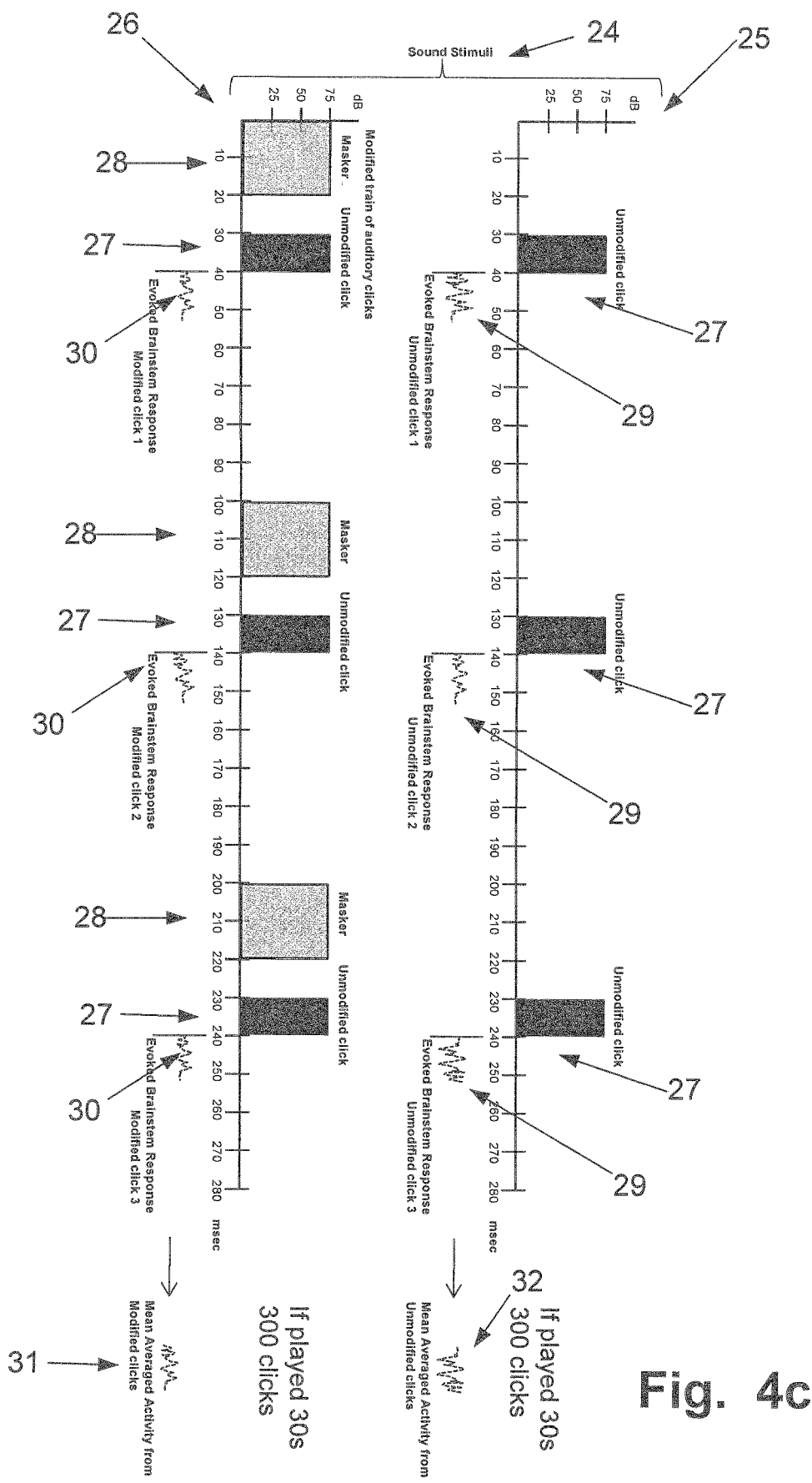
FIG. 4c is for an illustrative purpose showing a generated sound stimuli comprising of two trains having an arbitrary number of sound pulses and wherein the second train is modified by being preceded by masking noise.

FIG. 4c illustrates a further example of sound stimuli 24 that may be used according to some embodiments of the invention. The sound stimuli 24 comprises of two trains of sound pulses 25, 26, the upper is a first train of unmodified sound pulses 25 and the lower is a second train of modified sound pulses 26. Each unmodified sound pulse 27 is in this example an unmodified square shaped click having 10 ms duration. The modified sound pulse is a modification of the unmodified click 27 by having a the square shaped click similar to the unmodified click 27 being preceded by masking noise 28 having a duration of, in this example, 20 ms. Each unmodified or modified sound pulse will give rise to a evoked brainstem response 29, 30 respectively.

With reference to FIG. 4a, each block illustrating a first train of unmodified sound pulses 11 may comprise a single unmodified sound pulse 27 as of the upper part of FIG. 4c. In this example, after the single unmodified sound pulse 27 of the first train of sound pulses 25 is presented to the subject, a trigged recording of the evoked brainstem response 29 will be obtained, i.e. a first response signal.

Alternatively, each block in FIG. 4a illustrating a first train of unmodified sound pulses 11 may comprise a plurality of unmodified sound pulses 27 as of the upper part 25 of FIG. 4b. The plurality of sound pulses may thus comprise a number of sound pulses, such as in the range of 1 to 1000 unmodified sound pulses 27. Practical examples of numbers of unmodified sound pulses 27 may comprises defined numbers within this range, such as 3, such as 10, such as 50, such as 500. In the example given in FIG. 4c the first train of unmodified sound stimuli 25 comprises of 300 unmodified sound pulses 27 which will take about 30 sec to send to the subject and record trigged evoked brainstem responses 29 corresponding to each of the 300 unmodified sound pulses 27. Thereafter a mean average activity 32 is calculated from the, in the example, 300 evoked brainstem response signals 29 corresponding to each unmodified sound pulse 27 of the first train of unmodified sound pulses 25, i.e. the mean average activity 32 may be a first response signal.

With reference to FIG. 4a, each block illustrating a second train of modified sound pulses 12 may comprise a single modified sound pulse, i.e. a unmodified click 27 preceded by a masker 28, as of the lower part 26 of FIG. 4c. In this example, after the single modified sound pulse of the second train of sound pulses 26 is presented to the subject, a trigged recording of the evoked brainstem response 30 will be obtained, i.e. a first response signal.

Alternatively, each block in FIG. 4a illustrating a second train of modified sound pulses 12 may comprise a plurality of modified sound pulses, i.e. a sound pulse being an unmodified click 27 preceded by a masker 28, as of the lower part 26 of FIG. 4b. The plurality of sound pulses may thus comprise a number of sound pulses, such as in the range of 1 to 1000 modified sound pulses. Practical examples of numbers of modified sound pulses may comprises defined numbers within this range, such as, such as 3, such as 10, such as 50, such as 500. In the example given in FIG. 4c the second train of modified sound pulses 26 may comprise of 300 modified sound pulses which will take about 30 sec to send to the subject and record trigged evoked brainstem responses 30 corresponding to each of the 300 modified sound pulses. Thereafter a mean average activity 31 is calculated from the, in the example, 300 evoked brainstem response signals 30 corresponding to each modified sound pulse of the second train of modified sound pulses 26, i.e. the mean average activity 31 may be a first response signal.

By using sound stimuli comprising a plurality (herein 300 for exemplary purpose only) of sound pulses according to either example illustrated in FIG. 4b or c the sequence in FIG. 4a may be:

At $t_0$, generating and sending a first train of 300 unmodified sound pulses 11 to a subject (at this stage not under influence of substance or compound being tester or evaluated). For each of the 300 unmodified sound pulses of the first train 11 a response signal is obtained by a trigged recording and then there may be a gap before next unmodified sound pulse is sent so as to not having the recorded response signal being affected by temporal integration. The sending of the 300 unmodified sound pulses and recording of response signals thereof will take approximately 30 sec. Thereafter a mean average activity of the recorded evoked brainstem responses, i.e. first response signal 90, will be calculated at time $t_1$.

At $t_1$, generating and sending a second train of 300 modified sound pulses 12 to a subject (at this stage not under influence of substance or compound being tester or evaluated). For each of the 300 modified sound pulses a response signal is obtained by a trigged recording and then there may be a gap before next modified sound pulse is sent so as to not having the recorded response signal being affected by temporal integration. The sending of the 300 modified sound pulses and recording of response signals thereof will take approximately 30 sec. Thereafter a mean average activity of the recorded evoked brainstem responses i.e. second response signal 91, will be calculated the time $t_2$.

At $t_2$, the first and second response signal 90, 91 will be compared 12 and a degree of effect in a certain brainstem structure of a certain state 14 will be obtained for a subject not under influence of a substance or compound.

At $t_2$, the generating and sending of a sound stimuli comprising the same first and second train of sound pulses 11, 12 as above and obtaining a first and second response signal 90, 91 thereof will then be repeated.

At $t_4$ a new comparison 13 between the obtained mean averaged first and second response signals 90, 91 will be conducted and a new degree of effect in a certain brainstem structure of a certain state 14 will be obtained. In this example, at $t_4$ the subject is administered a substance or compound which effect on the subject will be tested. The generating and sending of sound stimuli comprising the same first and second train of sound pulses 11, 12 as above and obtaining a first and second response signal 90, 91 thereof will then be repeated.

At $t_6$, the first and second mean average response signal 90, 91 will be compared 13 and a degree of effect in a certain brainstem structure of a certain state 14 will be obtained for a subject under influence of a substance or compound. In this example an increase in a degree of effect in a certain brainstem structure of a certain state could be seen.

At $t_6$, the generating and sending of sound stimuli comprising the same first and second train of sound pulses 11, 12 as above and obtaining a first and second response signal 90, 91 thereof will then be repeated. At $t_8$ a new comparison 13 between the obtained mean averaged first and second response signals 90, 91 will be conducted and a new degree of effect in a certain brainstem structure of a certain state 14 will be obtained. In this example a decrease in a degree of effect in a certain brainstem structure of a certain state compared to the state at $t_6$ is seen. Thus this may be an indication that the compound or substance being metabolized.

The generating and sending of sound stimuli and obtaining of trigged recordings of response signals thereof may be further repeated over a certain period of time. The measuring procedure may then be halted and continued at another session.

The repeatedly sending of sound stimuli during one measuring session may be conducted in a consecutive sequence.

The comparison 13 of the first and second response signal 90, 91 corresponding to a first and second train of sound stimuli 11, 12 of each sound stimuli, provides the hereinbefore mentioned important self-reference of a subject. Further, in this example the degree of effect in a certain brainstem structure of a certain state 14 obtained at $t_2$ and $t_4$ is what hereinbefore has been referred to as the baseline of the subject.

The sending of the sound stimuli to a subject could be conducted to one ear at a time or both ears simultaneously for obtaining a lateral brainstem response state development.

Figure 5A:
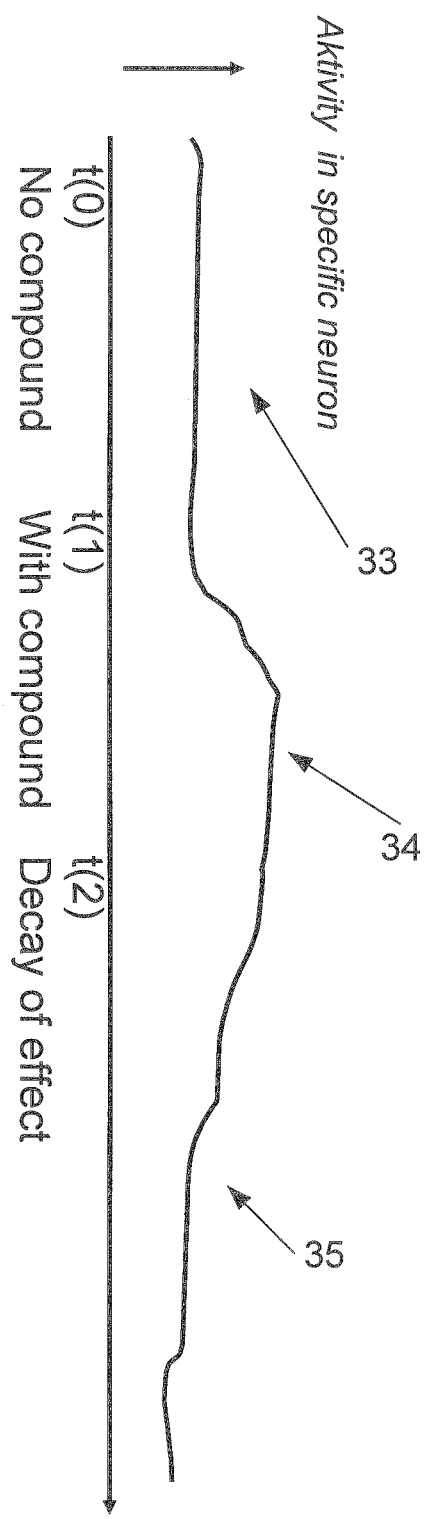
FIG. 5a is a graph that shows an arbitrary one neuron pharmacokinetic plot.

In an embodiment of the invention according to FIG. 5a a real-time study and monitoring of the short term effect of subject after the subject has been delivered a compound, substance or food (pharmacokinetic) is illustrated. In FIG. 5a the development of a lateral brainstem response state is only presented for one neuron but in alternative and/or additional embodiments of the invention this may be performed for more than one neuron simultaneously (topography).

The test starts at t(0) by establishing a baseline 33 for the subject. The baseline may be established by repeatedly generating and presenting sound stimuli to a subject, not under influence of a psychoactive compound, substance or food.

Alternatively, the subject may be under influence of a psychoactive compound, substance or food when obtaining the baseline 33. The dosage and/or psychoactive compound, substance or food or dosage should then differ from the dosage and/or psychoactive compound, substance or food which effect on the subject is to be studied.

Additionally and/or alternatively, the subject may have been administrated a placebo before and or/during the establishing of a baseline 33.

By recording the response signals, connected to a first and at least a second train of sound pulses of sound stimuli, from a subject when not under influence of a psychoactive compound, substance or food, during a period of time starting at t(0) a baseline 33 representing the normal activity of the lateral brainstem response state of the subject being tested is established. If each train of the sound stimuli comprises more than one sound pulse a mean average of the brainstem response may be used to establishing baseline.

In some embodiments of the invention the baseline 33 may be used to establish a baseline for a placebo for a subject.

At the time t(1) the subject will be delivered or administrated a psychoactive compound, substance or food. This may in some cases be a placebo. This may give rise to a response 34 connected to one or more of the neurons. In some embodiments of the invention the response 34 is measured as a percentage to the baseline of the subject.

The sound stimuli repeatedly generated and sent to a subject, during the monitoring of the effect of a psychoactive compound, substance or food, are the same sound stimuli as when the baseline 33 was established comprising a first and at least a second consecutive train of sound pulses.

If the trains of sound pulses comprised more than one sound pulse during the establishing of a baseline 33 the trains of sound pulses after t(1) could be focused to only comprise parts the trains of sound pulses used to establishing the baseline 33. Thus shortening the time and receive a better time resolution may be provided. In these cases the sound pulses known to evoke a response in the neurons of interest are being picked. The same effect of a higher time resolution may also be received when the establishing of a baseline 33 is performed using only one or more sounds that are of interest to the neurons being studied.

At t(2) the effect of the psychoactive compound, substance or food starts to decay 35, for example due to The substance or compound being metabolized.

The period of time for a session of real-time monitoring (pharmacokinetic) is usually shorter than 2 hours and preferably around 40 minutes but in some instances it may be as short as a few minutes such as 1 to 10 minutes. The session could be longer than 40 minutes if the effect of a psychoactive compound, substance or food that needs to be studied during a longer period of time. Preferably the time for a single session is in the time range of 20 minutes to 2 hours.

Figure 5B:
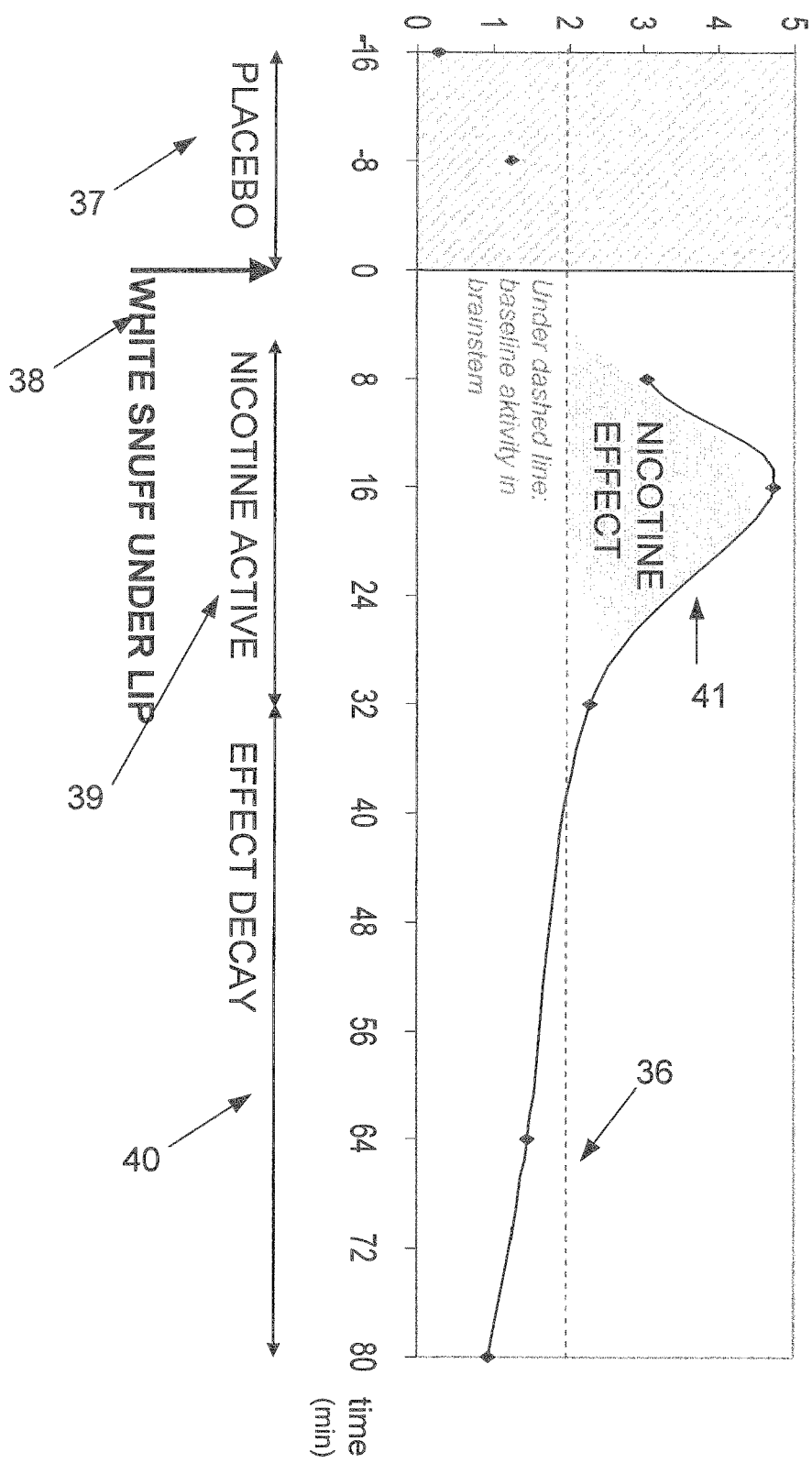
FIG. 5b is a graph that shows a pharmacokinetics plot over the influence of nicotine on one specific neuron of a subject.

In FIG. 5b the influence of nicotine 41, e.g. white snuff, to a subject being tested is shown. If this plot was to be compared to a plot when using a standard method i.e. plasma, the effect of nicotine 41 in the plasma plot would be delayed and would appear to the right of the peak seen in the plot. Thus the invention may be a much more accurate technique since the peak 41 appears much closer to when the subject starts to experience the effect of a psychoactive compound, substance or food.

In this plot the dashed line shows the baseline activity 36 in the brainstem of the subject being tested. Measurements of activity of at least one brainstem neuron by using the invented device, system and methods were conducted at around 16 minutes and 8 minutes before the subject was delivered the white snuff under the lip 38. In this example, the subject was using a placebo during the time period 37 of establishing a baseline 36. The activity of the brainstem neuron was then measured at 0, 8, 16, 32, 64 and 80 minutes after white snuff was placed under the lip 38. The nicotine effect 41 may be seen during the nicotine active phase 39 between 0 to 32 minutes where after the effect of nicotine is decaying 40.

Figure 5C:
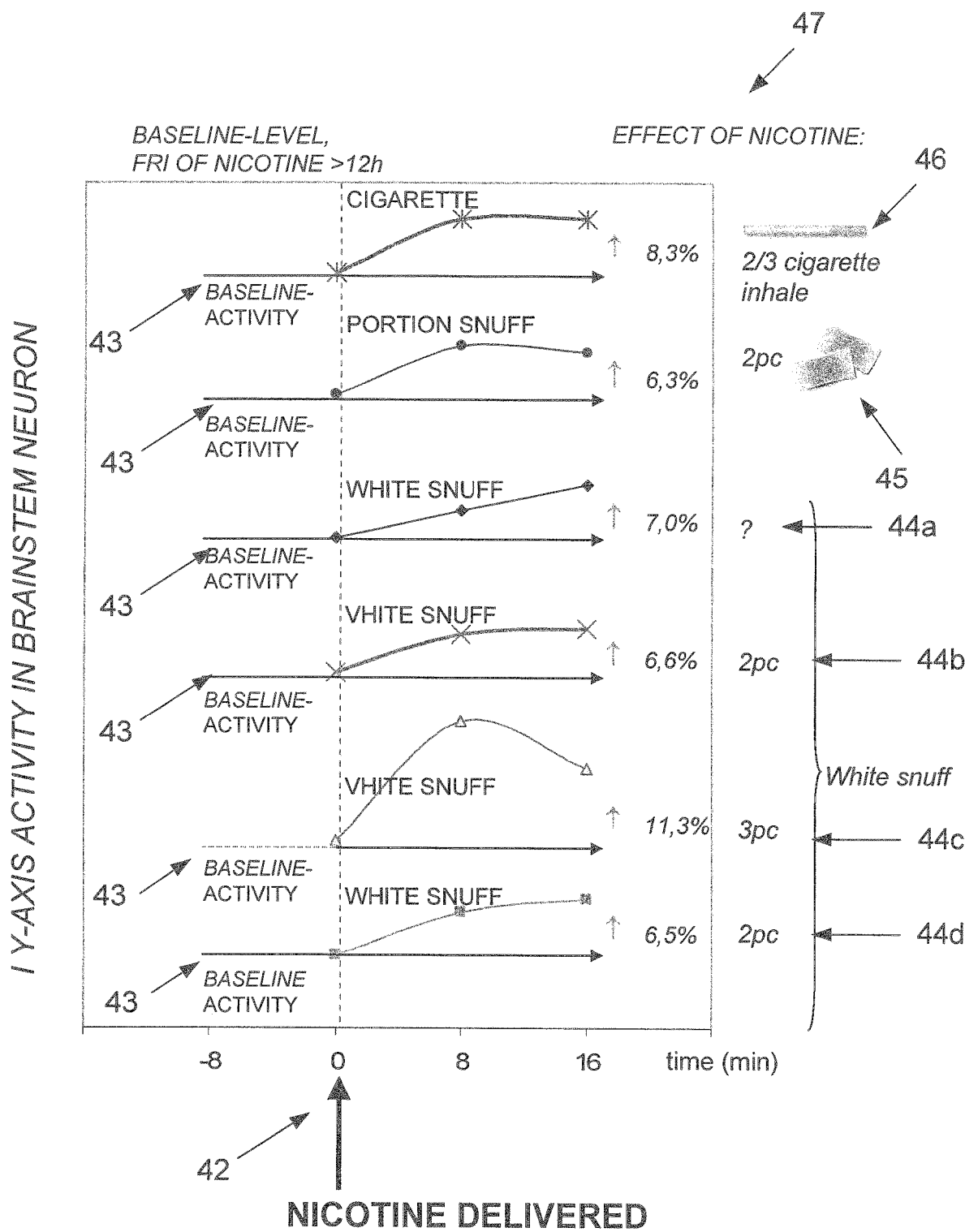
FIG. 5c is a graph that shows pharmacokinetic plots over different nicotine products and the effect of the products on different subjects.

FIG. 5c shows the effect of different nicotine products 47 on six different subjects. The individual effect of a nicotine product on each subject is shown as an activity in brainstem neuron as a percentage compared to an, for each subject, individual baseline activity 43. The baselines 43 were established for each subject after the subject has shown to be free of nicotine for more than 12 hours. Nicotine was delivered 42 to each subject at time point 0. The plots shows from top to bottom: a subject smoking ⅔ of a cigarette by inhaling 46; a subject placing 2 pcs of portion snuff under the lip 45; a subject placing an unknown amount of white snuff under the lip 44a; a subject placing 2 pcs of white snuff under the lip 44b; a subject placing 3 pcs of white snuff under the lip 44c; and a subject placing 2 pcs of white snuff under the lip 44d. The result in each plot is shown as a percentage of the effect of nicotine compared to the baseline of each test subject.

Figure 6A:
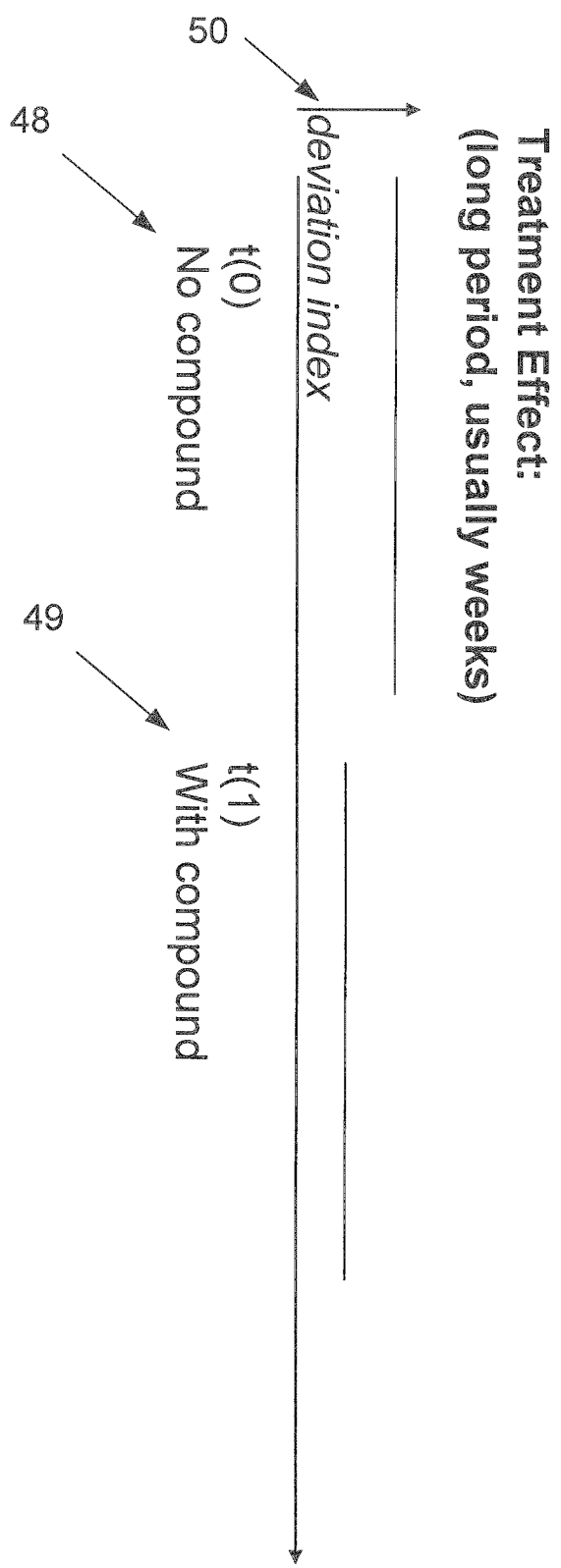
FIG. 6a is a graph that shows an arbitrary long term effect plot.

A further embodiment of the invention is illustrated in FIG. 6a wherein the long term treatment effect of a psychotropic compound or substance or food on a subject is illustrated schematically.

A first session at t(0), lasting a period of time, was performed to establish a baseline of the subject to which the effect of a compound could be compared to obtain a deviation index 50. The establishing of the baseline is done the same way as previously mentioned using the invented device and method. In this example, when establishing the baseline the subject was not under influence of a psychotropic compound or substance or food 48. The subject is then delivered a psychotropic compound or substance or food 49. A second session, lasting a period of time, was performed at t(1). This second session occurred either a day, such as days; or a week, such as weeks, or a month, such as months, after the first session. The subject, now under influence of a psychotropic compound or substance or food or a placebo, is again presented with repeated sound stimuli in a similar way as previously described regarding short term effects FIG. 5a-c (pharmacokinetic).

In some embodiments when evaluating a long term related effect, such as a treatment effect, the effect on the brainstem response (measured values) may be averaged over the whole period of time for each session.

Additionally and/or alternatively, further subsequently performed sessions may be conducted. Thus the long term treatment effect of a psychotropic compound or substance or food on a subject can be studied. Usually these sessions take place under a time period of weeks but could also be months or years.

Additionally and/or alternatively, subsequently performed measuring sessions could be used to establish a baseline of the subject.

Additionally and/or alternatively, each conducted measuring session may be evaluated in real-time. In addition, in some embodiments of the invention, when evaluating the brainstem response of each session in real-time an average of the response over the whole session may be established and used for the long-term evaluation of the effect.

A complete measurement session may, in some embodiments, last around 40 minutes, depending on the sound stimuli used. The session may in some embodiments be shorter by focusing the sound stimuli so that each train includes fewer sound pulses closely connected to the neurons of interest.

The measuring time of the invention can be kept short in embodiments since no rejection of insufficient measurements may be made during the measurements session, as normally was done previously. Instead, due to the vast amount of sound stimuli presented to the subject during a session, corrupt data may be refused during the analysis process. Corrupt data may be identified by thresholding the measured values to be within a typical range thereof.

Figure 6B:
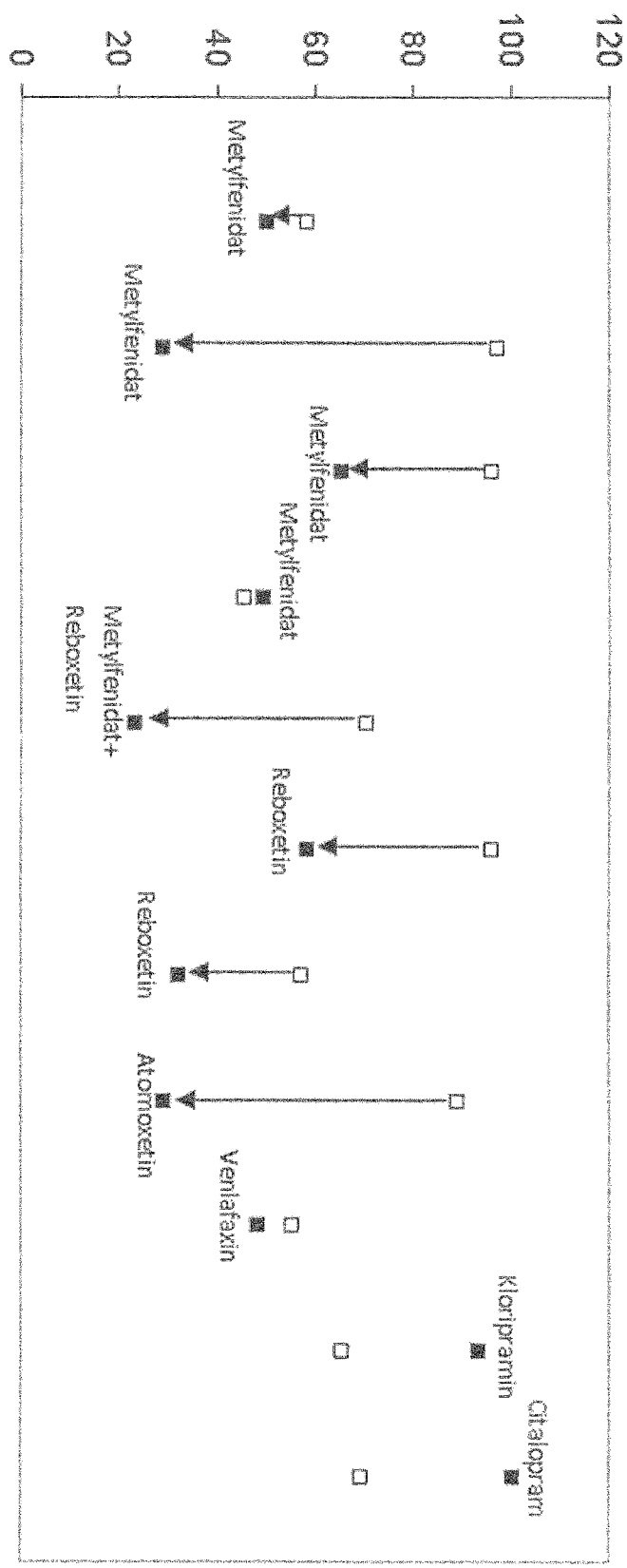
FIG. 6b is a graph that shows the long term effect on a subject diagnosed with ADHD while presented with different medication.

In FIG. 6b an example is illustrating the long term effect on 11 subjects diagnosed with ADHD and presented with different medications. The white square represents the baseline or deviation index of each subject while the black box represents the activation of the lateral brainstem response state at a later session when the individual is undergoing treatment using a medication. From the plot it is evident that medication known for having an effect on subjects diagnosed with ADHD lowers the average activity of the lateral brainstem response state for the related neurons. In contrast medications known for their effect on subjects diagnosed with depressions is here raising the activity of the average lateral brainstem response state.

Embodiments of the innovation pertain to recording of bilateral activity, meaning evoked responses from both sides of the brainstem, ipsilateral activity, meaning only activity on the same side as stimulation, contralateral activity, meaning activity on the side which sounds are not presented, or any combinations of mentioned conditions. Thus complex lateral and topographic response profiles may be established in relation to a specific investigated state.

This may be conducted by presenting the same stimuli to both ears either simultaneously or alternatingly one ear at a time. Alternatively different sounds stimuli may be used for each ear.

These lateral variation response profiles provide for the possibility to investigate and determine how a certain administered substance influences function of a defined topographical position in the brainstem. For instance it can be shown that a certain substance only influences a single side of the brainstem. An example is that the right brainstem side is activated by the substance, but not the left side. The above recording of bilateral activity, ipsilateral activity, or contralateral activity may be provided by stimulating only one of the ears at a time while measuring the activity of both brainstem sides as well as determining how a substance influences this response. A ratio of left/right ear stimulation in relation to the left/right brainstem side may be provided as measurement data.

Figure 7:
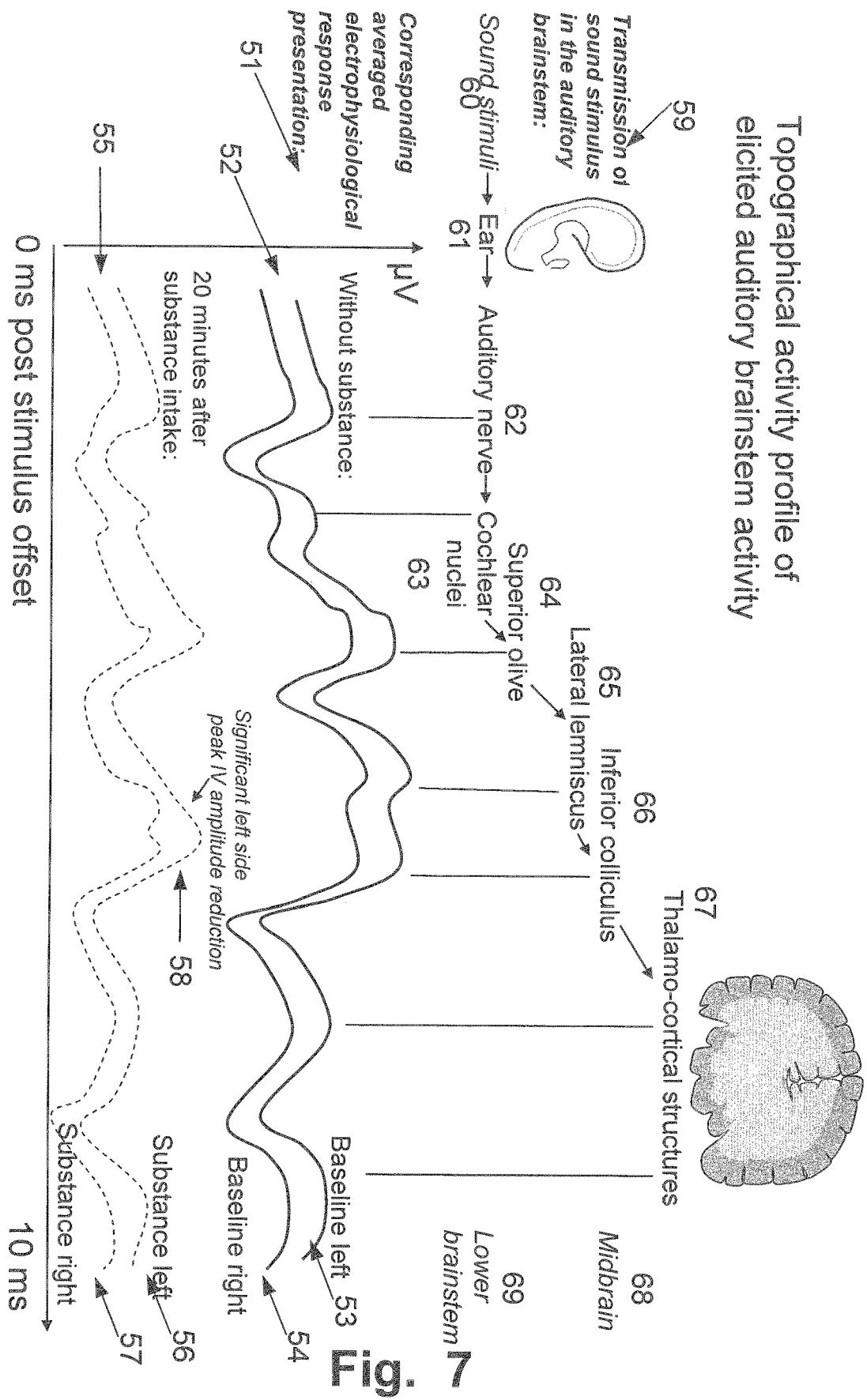
FIG. 7 is a graph that shows a typical example of an arbitrary topography plot.

FIG. 7 is illustrating an example of an arbitrary topographical activity profile 51 of, in this example, elicited auditory brainstem activity. The response is in this example measure using a trigged recording over a 10 ms time range post stimulus. Topography makes it possible to investigate where a certain psychotropic compound or substance or food is active and where an effect may be shown. This can be performed either as a short time (pharmacokinetic) session or during a long term treatment effect series of measurements. In both cases more than one neuron is evoked and the lateral brainstem response state is determined. The development of the lateral brain stem response state for more than one neuron is then analyzed. The activity of the neurons can be plotted in the same graph to show where a psychotropic compound or substance or food is having an active effect and how strong the effect of the psychotropic compound or substance or food is. The topography plot may also show differences between the responses between the left and right side.

In FIG. 7 the solid lines 52 show a corresponding averaged electrophysiological response presentation of left side 53 (top) and right side 54 (bottom) of a subject without being under influence of a substance or a compound. Thus these two solid lines 52 represents baseline of the subjects the left and right side 53, 54 of the brainstem response, respectively. The dashed lines 55 show the left 56 (top) and right 57 (bottom) side of the brainstem response of a subject 20 minutes after intake of a substance. As can be seen there is a significant lefts side peak IV amplitude reduction. 58

Further, FIG. 7 is also illustrating more specifically how the changes in activity due to a substance delivered to a subject alters only specific areas of the brainstem. In the example of FIG. 7 only a specific group of neurons is affected on one side of the brainstem. Thus a topographic representation, combining the fact that the test subject is his own reference (use of an unmodified train of sound pulses and a consecutive modified train of sound pulses) with the use of an individual baseline (see baseline curves versus substance affected curves), with a high resolution topographical display revel of details makes tracing of the compounds effect easy. Furthermore, complex sound stimuli is most commonly needed in order to detect brief deviances in the brain's coding mechanisms, which might not be indicated with a standard auditory stimulus.

For clarity the curve the transmission of sound stimuli in the auditory brainstem 59 is shown. First sound stimuli 60 is presented to the ear 61 which will have an effect on the auditory nerve 62; then the Cochlear nuclei 63; then the Superior olive 64; then the Lateral lemniscus 65; then the Inferior colliculus 66; and last the Thalamo-cortical structures 67. Thus the sound stimulus may in this example evoke responses from the lower brainstem 69 to the midbrain 68.

Figures 8A, 8B:
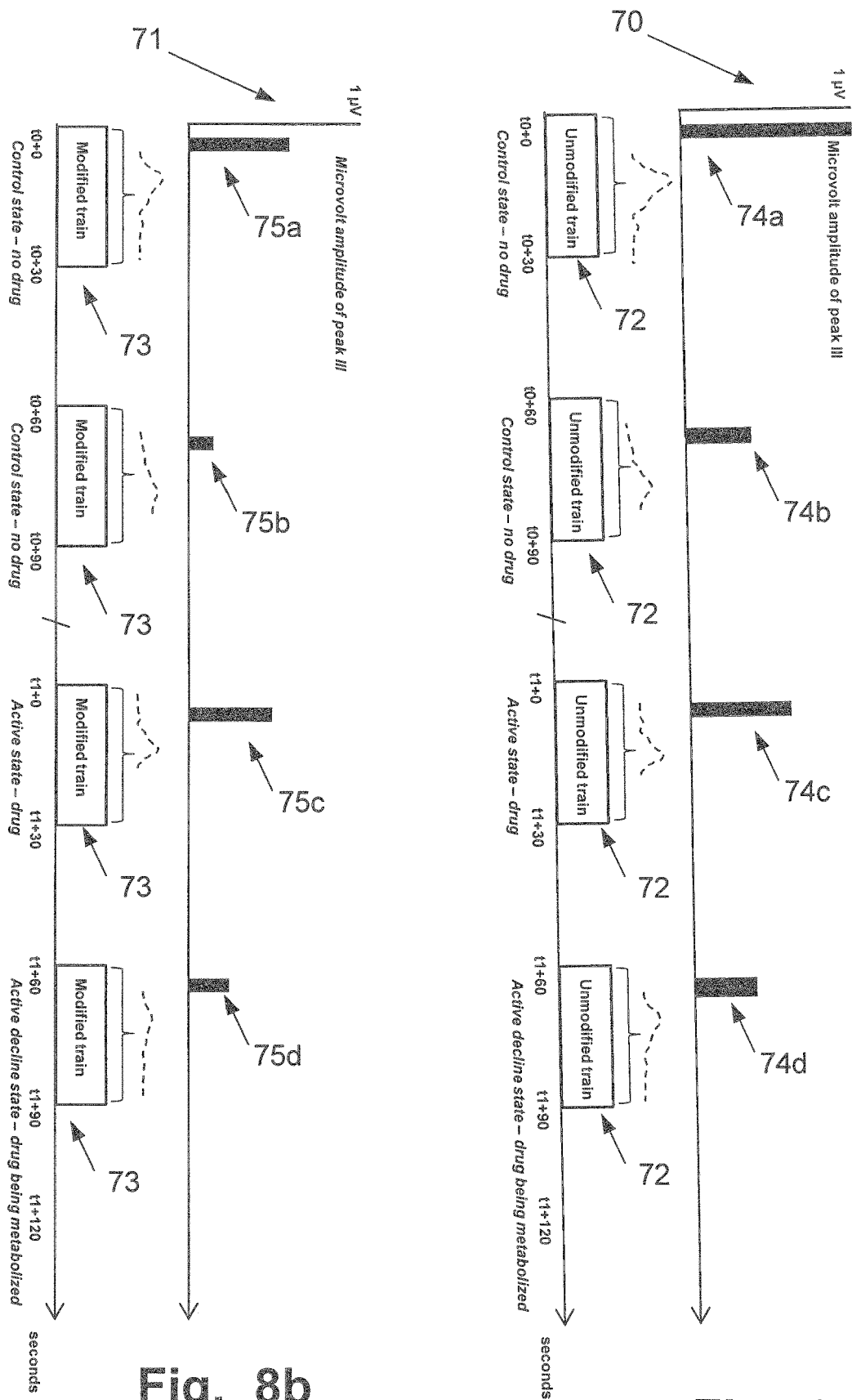
FIG. 8a is showing a testing of the effect of oral methylphenidate medication in a patient with ADHD where the measuring was conducted using only unmodified sound pulses similar to the pulses of a first train.
FIG. 8b is showing a testing of the effect of oral methylphenidate medication in a patient with ADHD where the measuring was conducted using only modified sound pulses similar to the pulses of a second train.
Figure 8C:
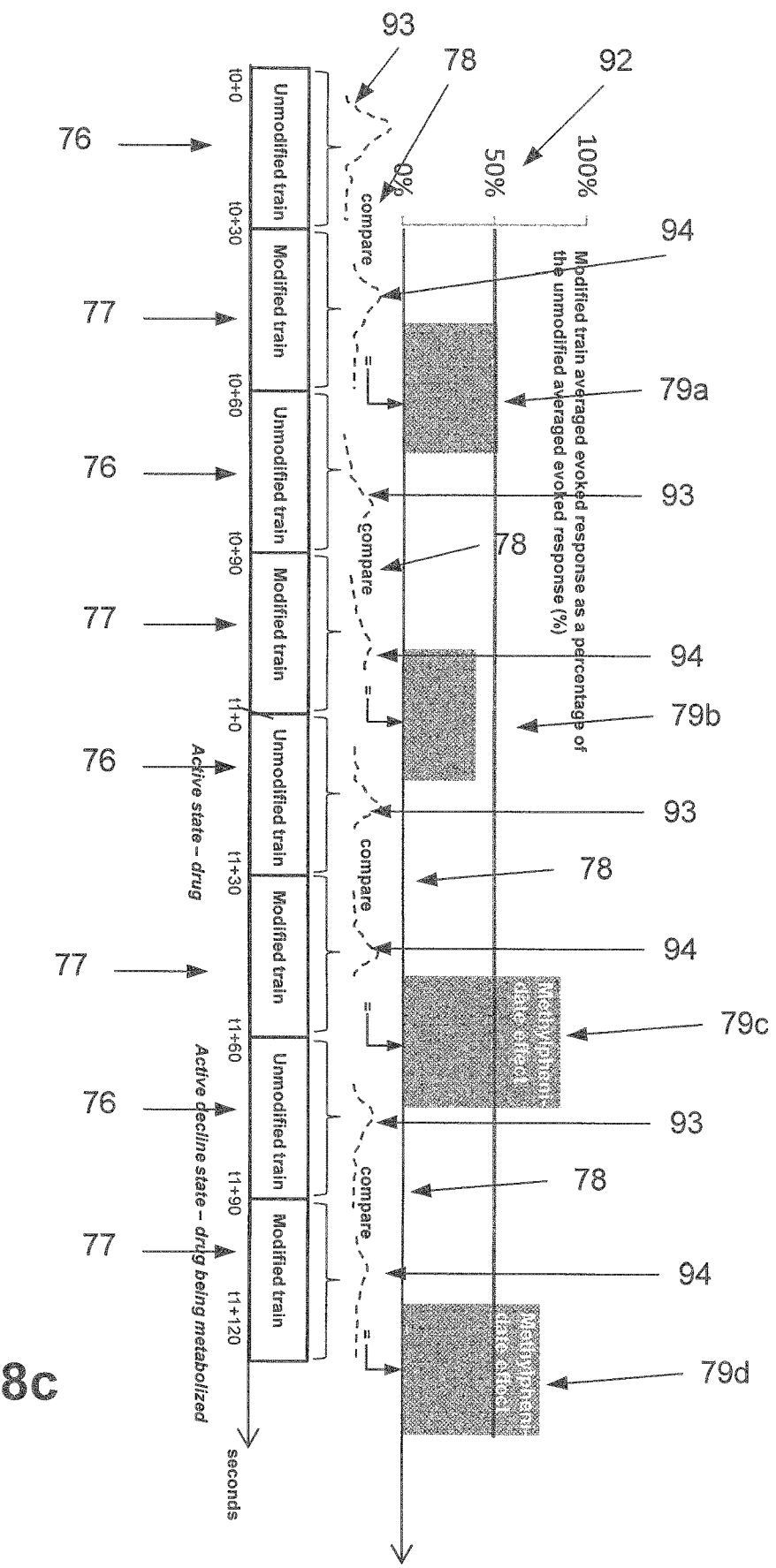
FIG. 8c is showing a testing of the effect of oral methylphenidate medication in a patient with ADHD where the measuring was conducted using repeatedly presented sound stimuli according to the invention wherein the sound stimuli comprising a train of unmodified sound pulses followed by a train of modified sound pulses.

To emphasize the importance of using the subject as its own reference when conducting herein described tests, FIG. 8a-c is showing a test of the effect of oral methylphenidate medication in a patient with ADHD. In this test each of the train of sound pulses will repeatedly present sound pulses to the patient for thirty seconds and for each sound pulse presented to the subject a corresponding response signal is recorded. The response signal for each set of train of sound pulses is then averaged to obtain an evoked averaged brainstem response. The measuring starts at t0 for a drug free control measurement of the patient (i.e. establishing an individual baseline of the patient). t1 is the time after the oral methylphenidate was consumed and had passed out to plasma.

In FIG. 8a, a measuring with only unmodified sound pulses, i.e. the sound stimuli comprising only one train being a train of unmodified sound pulses 72. Sound stimuli were presented twice to the subject (at t0+0 and t0+60 sec) and the corresponding response signals were recorded and evoked averaged brainstem responses were established 74a, 74b. This was done when the patient was not under influence of methylphenidate medication, i.e. baseline or control state. The measured variable is here an absolute value 70 measured in μV of the amplitude of peak III. After the methylphenidate was consumed the sound stimuli (same 30 sec train of unmodified sound pulses 72) were presented to the patient at the active state of the drug at t1+0 and again at the active state when the drug is being metabolized at t1+60 sec. Both times the corresponding response signals were recorded and evoked averaged brainstem responses were established 74c, 74d. In this measurement no detectable methylphenidate effect could be established.

In FIG. 8b, a measuring with only modified sound pulses, i.e. the sound stimuli comprising only one train being a train of modified sound pulses 73. Sound stimuli were presented twice to the subject (at t0+0 and t0+60 sec) and the corresponding response signals were recorded and evoked averaged brainstem responses were established 75a, 75b. This was done when the patient was not under influence of methylphenidate medication, i.e. baseline or control state. The measured variable is here an absolute value 71 measured in NV of the amplitude of peak III. After the methylphenidate was consumed the sound stimuli (same 30 sec train of modified sound pulses 72) was presented to the patient at the active state of the drug at t1+0 and again at the active state when the drug is being metabolized at t1+60 sec. Both times the corresponding response signals were recorded and evoked averaged brainstem responses were established 75c, 75d. In this measurement no detectable methylphenidate effect could be established.

In FIG. 8c, a measuring of relative effect 92 with repeated sound stimuli comprising a first train of unmodified sound pulses 76 and a consecutive second train of modified sound pulses 77. The sound stimuli were presented twice to the subject (at t0+0 and t0+60 sec). For each train of sound stimuli the corresponding response signals was recorded and evoked averaged brainstem responses were established 93, 94. Thus a first averaged response signal 93 for each first train of unmodified sound pulses 76 and a second averaged response signal 94 for each second train of modified sound pulses 77 were obtained. At t0+60 and at t1+0 sec the first and second averaged response signals 93, 94 corresponding to the sound stimuli presented to the patient at t0+0 and t0+60 sec, respectively, was compared 78. These two sound stimuli were presented when the patient was not under influence of methylphenidate medication, i.e. control state or baseline. The measured variable is presented as a modified train averaged evoked brainstem response as a percentage of the unmodified average evoked response 79a, 79b. After the methylphenidate was consumed the same sound stimuli was presented to the patient at the active state of the drug at t1+0 and again at the active state when the drug is being metabolized at t1+60 sec. Again the corresponding response signals was recorded and first and second averaged response signals 93, 94 for each train of sound pulses of each sound stimuli was established. The first and second average response signals 93, 94 were compared 78 at t1+60 sec and t1+120 sec. Now a detectable methylphenidate effect could be seen 79c, 79d. Hence the conclusion may be that to trace the effect of, in this case, methylphenidate the presented invented device and method is needed.

Figure 9:
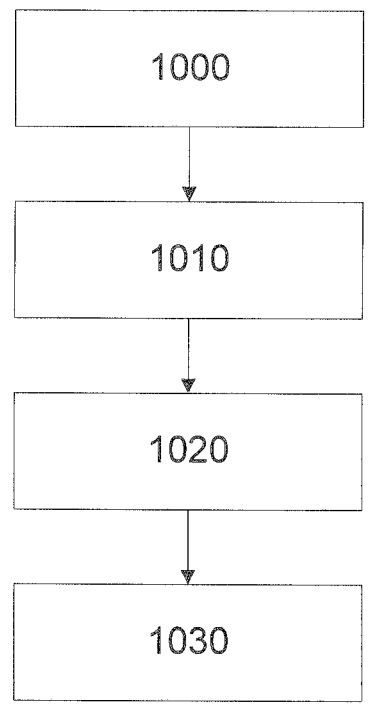
FIG. 9 is a flowchart that shows the use of embodiments for obtaining and processing brainstem pattern profiles.

In further embodiment, being illustrated in FIG. 9, the device or method for detecting a lateral brainstem response state development of a subject is used for blind identification of a substance through brain pattern analysis. To this end the later brainstem response state is the complex data obtained using the method previously described where the test subject is his own reference by employing a method based on sound stimuli comprising a first train of unmodified sound pulses and at least one trains of modified sound pulses wherein the second train is being consecutive to the first train.

The method may be performed in many different ways. For example, all 13 sound pulses may be used in at least two consecutive trains of sound pulses. By repeatedly presenting the sound stimuli to a subject a complex evoked lateral brainstem response state pattern will be obtained 1000 that results in a brainstem response profile (see FIG. 1) of the activity of the subjects population of neurons. By applying different modulations and/or modifications to the sound pulses of the second train of sound pulses i.e. first repeatedly run the test with a first modulation for a certain first period of time and then again with a different modulation for a second period of time and then with a third type of modulation and so on. By comparing the recorded profiles with data from a database 1010 comprising information from a population of profiles obtained from a large group of subjects being under influence of a different psychotropic compound, substance, or foodstuff, an overlap between the subject's profile and the compiled data in the data base will be found 1020. The overlap will indicate what active psychotropic compound or substance the tested subject is under influence under 1030.

The test may be focused to a specific or a group of psychotropic compound(s) or substance(s) or foodstuff by only including sound stimuli and modifications of the sound stimuli known to evoke lateral brainstem response state for the specific psychotropic compound or substance or group of psychotropic compounds or substances.

The same method may be used for obtaining brainstem profiles of patients and identify corresponding treatment, i.e. a specific drug, known to have positive effects. This may be done by obtaining a patients brainstem pattern profile 1000 and comparing it 1010 to a database of known patterns and pharmaceutical drugs known to have positive treatment effect on a patient with a specific type of brainstem pattern profile.

The comparison will give an overlap 1020 that can be used to a first identification of a suitable drug for a patient with a brainstem pattern profile 1030. This may helping a medical practitioner to increase the therapeutic efficiency of a therapy by choosing the most effective drug and/or dosage to a specific patient. Hence a decrease may be provided of the time spent for trying different drugs on a patient before finding one that works well. Thus lowering the time a patient may have to suffer due to, for the patient, wrong medication and/or dosage or use of a medication and/or dosage with low effect This could also help to lowering the risk of the patient to experience side-effects.

These methods are here described in qualitative terms but the invention may also be used to run the same test quantitative.

The method may comprise modifying the sound pulses, forming the second train of sound pulses, comprising adding noise before, after or on top of each sound pulse of the train of sound pulses; and/or by increasing and/or lowering the frequency and/or amplitude of the second train of sound pulses.

The method may comprise providing a reference value for the subjects lateral brainstem response state based on the first response signal.

The method may comprise detecting a second response signal corresponding to the at least one second train of sound pulses and comparing the first response signal to the reference value of the subject for determining the lateral brainstem response state.

The method may comprise repeatedly generating and sending the sound stimuli comprising at least two consecutive trains of sound pulses to the subject, not being under influence of a psychotropic compound or substance or food, and thus establishing a lateral brainstem response state baseline of the subject to the second train of sound pulses.

The method may comprise repeatedly generating and sending the sound stimuli to the subject, and monitoring and determining a subject's brainstem response state development by comparing a current the brainstem response state to the baseline in real-time during a measurement session lasting a first period of time and wherein the subjects brainstem response state development is a comparison to the baseline of the subject.

The method may comprise determining a short time effect or influence of a psychotropic compound or substance or food or a placebo on the subject.

The method may comprise repeatedly generating and sending the sound stimuli to the subject during a first measurement session and then subsequently, during a second period of time, at least a second measurement session occurring at a later occasion, wherein a subjects brainstem response state development is determined over the second period of time by comparing the current brainstem response state to the earlier established baseline of the subject.

The method may comprise determining a long term treatment effect or influence of a psychotropic compound or substance or food or a placebo on the subject.

The method may comprise monitoring different neurons responses to different sound stimuli simultaneously.

In the method the detected lateral brainstem response state of a subject may be a profile of a lateral brainstem response state of the subject.

The method may comprise comparing the profile of a subject to a database comprising a population of profiles determines if the subject is under influence of a psychotropic compound or substance or food.

The method may comprise determining the psychotropic compound or substance or food quantitatively.

In an embodiment, a computer-readable medium having embodied thereon a computer program for processing by a computer, such as comprised in the afore described system, is provided for detecting a lateral brainstem response state development of a subject over a period of time as a function of a population of neurons evoked response patterns to sound stimuli, the computer program comprising a plurality of code segments comprising a first code segment for repeatedly presenting the subject with a sound stimulus evoking the neurons response patterns wherein the sound stimulus comprising a first and at least a second consecutive train of sounds pulses; a second code segment for revoking a first response signal by the first train of sound pulses and evoking a second response signal by the second train of sound pulses; a third code segment for detecting a brainstem response signal related to the neurons response patterns; and a fourth code segment for determining the lateral brainstem response state development based on a comparison between the first and second response signals.

The computer program may be provided for enabling carrying out the afore described a method.

Use of, or a method of using, an audiometry brainstem response system, or of the afore described system, or the afore described method may be provided for detecting an effect of a substance on the brain of a person based on differences in obtained responses. The substance may be a psychoactive compound and the effect is caused by the psychoactive compound. The substance may be food and the effect is caused by the food. The substance may be a medical drug and the effect is caused by the medical drug. The substance may be a chemical substance administered to the person and the effect is caused by the chemical substance. The substance may be an herbal compound and the effect is caused by the herbal compound. The substance may be a gas inhaled by the person and the effect is caused by the gas. The substance may be a fragrance to which the person is subject to and the effect is caused by the fragrance.

The use or a method of using may comprise determining when a person starts to perceive the effect. The effect may be determined before the subject is aware of the effect.

Use of, or a method of using, an audiometry brainstem response system, or of the afore described system, or the afore described method may be provided for detecting when a medication has an effect on a person. The medication may be an ADHD medication and the effect is detected by detecting a lowered average activity of the lateral brainstem response state for specific neurons.

Use of, or a method of using, an audiometry brainstem response system, or of the afore described system, or the afore described method may be provided for detecting a lateral brainstem response state development of a subject for blind identification of a substance through brain pattern analysis.

Use of, or a method of using, an audiometry brainstem response system, or of the afore described system, or the afore described method may be provided for monitoring neurophysiological effects of psychotropic compounds or substance or food or therapy in real-time.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A device adapted for blind identification of an active psychotropic compound, substance or foodstuff through brain pattern analysis by detecting lateral brainstem response states of a subject over a period of time as a function of a population of neurons' evoked response pattern to sound stimuli, comprising:
    a sound stimuli generating apparatus operative to repeatedly send, over a period of time, identical sound stimuli to said subject to evoke response patterns from a population of neurons in the brainstem, wherein each of said sound stimuli comprises a first train of unmodified sound pulses and at least one second consecutive train of modified sound pulses;
    a detector operative to detect a brainstem response signal related to said response patterns, wherein a first brainstem response signal is caused by said first train of sound pulses and at least one subsequent brainstem response signal is caused by said second consecutive train of modified sound pulses;
    a memory operative to store information based on said brainstem response signals;
    and a computer operative to repeatedly, over said period of time, determine said lateral brainstem response states for each of said sound stimuli, wherein said lateral brainstem response states are relative values based on comparisons between said first brainstem response signal and said at least one subsequent brainstem response signal of said sound stimuli;
    wherein said computer is adapted to generate a brainstem response profile of a subject based on said lateral brainstem response states of said subject; and,
    wherein said computer is adapted to make a comparison between said brainstem response profile and a database comprising information from a population of profiles obtained from a group of subjects being under an influence of a psychotropic compound, substance or foodstuff, and to determine an overlap such that the active psychotropic compound, substance or foodstuff is identified;
    wherein said device is configured to determine the active psychotropic compound, substance or foodstuff regardless of whether or not said subject is conscious.

2. The device according to claim 1, wherein said generated first train of sound pulses is a train of predetermined and fixed sound pulses comprising at least one sound pulse that is configured to evoke at least one of said neurons in the brainstem.

3. The device according to claim 1, wherein the generated second train of sound pulses comprises at least one modified sound pulse of said first train of sound pulses, wherein said at least one modified sound pulse is created by adding noise either before, after, or on top of said sound pulse of said first train of sound pulses; and/or said at least one modified sound pulse is created by an increased and/or decreased frequency, and/or amplitude in comparison to said sound pulse of said first train of sound pulses.

4. The device according to claim 1, wherein said computer is adapted to detect a development of said lateral brainstem response states over said period of time.

5. The device according to claim 1, wherein said computer is operative to determine an average first brainstem response signal and at least one average subsequent brainstem response signal from said first and said at least second train of sound stimuli when each of said first and said at least second train of sound comprise a plurality of sound pulses.

6. The device according to claim 1, wherein said computer is operative to monitor different neurons responses topographically.

7. The device according to claim 1 wherein said computer is adapted to determine said psychotropic compound or substance or foodstuff qualitatively.

8. The device according to claim 1 wherein said computer is further adapted to determine an effective therapy and/or treatment for said subject using the database.

9. A system for detecting a lateral brainstem response state development of a subject comprising a device according to claim 1;
    wherein said system is adapted to repeatedly generate and send, over a period of time being a first period of time, a sound stimulus comprising a first train of sound pulses and at least a second consecutive train of modified sound pulses to said subject; and
    wherein said system being operative to establish a lateral brainstem response state baseline of said subject as relative values based on comparisons between said first brainstem response signal and said at least one subsequent brainstem response signal of said sound stimulus repeated over said first period of time.

10. The system according to claim 9, wherein said system is adapted to repeatedly generate and send said sound stimuli over a second period of time to said subject after administration of a psychotropic compound or substance or foodstuff or a placebo or therapy;
    wherein a subject's brainstem response state development is monitored and determined by said system during a measurement session lasting said second period of time and wherein the determination of said subject's brainstem response state development is a comparison of a current lateral brainstem response state to said baseline of said subject.

11. The system according to claim 10, wherein said system is adapted to determine a short time effect or influence of the psychotropic compound or substance or foodstuff or a placebo or therapy on said subject's brainstem response state development.

12. The system according to claim 9, wherein said system is adapted to repeatedly generate and send said sound stimuli to said subject at least at a second measurement session subsequently conducted at a later occasion after a first session, and wherein said computer is operative to determine said subject's brainstem response state development as a comparison of a current lateral brainstem response state to said baseline of said subject, wherein said baseline is established at said first measuring session.

13. The system according to claim 9 wherein said system is adapted to determine a long-term treatment effect or influence of the psychotropic compound or substance or foodstuff or a placebo on said subject's brainstem response state development.

14. A method for blind identification of an active psychotropic compound, substance or foodstuff through brain pattern analysis by detecting lateral brainstem response states of a subject over a period of time as a function of evoked response patterns of a population of neurons in the brainstem to sound stimuli, wherein said method comprises:
  operating an apparatus for generation of stimuli for repeatedly presenting said subject with an identical sound stimulus, over said period of time, evoking said neurons' response patterns, wherein said sound stimulus comprises a first train of unmodified sound pulses and at least a second consecutive train of modified sounds pulses, wherein said second train of sound pulses comprising at least one modified sound pulse of said first train of sound pulses;
  evoking a first brainstem response signal by said first train of unmodified sound pulses and evoking a second brainstem response signal by said second train of modified sound pulses;
  operating a detector with an organ for registration of electrophysiological brain activity for detecting said first and second brainstem response signals related to said neurons response patterns;
  operating a computer for determining said lateral brainstem response states as relative values repeatedly, over said period of time, based on a comparison between said first and second brainstem response signals of each of said sound stimulus;
  generating a brainstem response profile of a subject based on said lateral brainstem response states of said subject; and,
  making a comparison between said brainstem response profile and a database comprising information from a population of profiles obtained from a group of subjects being under an influence of a psychotropic compound, substance or foodstuff, and
  determining an overlap such that the active psychotropic compound, substance or foodstuff is identified;
  wherein said subject may be conscious or unconscious.

15. The method according to claim 14, further comprising determining a development of said lateral brainstem response states over said period of time.

16. The method according to claim 14, further comprising determining an average first brainstem response signal and at least an average second brainstem response signal when each of said first and said at least second train of sound stimuli comprise a plurality of sound pulses.

17. The method according to claim 14, further comprising establishing a lateral brainstem response state baseline of said subject over a first period of time when said subject is not under the influence of a psychotropic compound or substance or foodstuff or therapy.

18. The method according to claim 17, further comprising:
  generating and sending, repeatedly, said sound stimuli, over at least a second period of time, to said subject after administration of a psychotropic compound or substance or foodstuff or a placebo or therapy;
  monitoring and determining said subject's brainstem response state development in real-time, during a measurement session, lasting said second period of time, and wherein the determination of said subject's brainstem response state development being a comparison of a current lateral brainstem response state to said baseline of said subject.

19. The method according to claim 18, further comprising determining a short time effect or influence of a psychotropic compound or substance or foodstuff or a placebo or therapy on said subject's brainstem response state development.

20. The method according to claim 17, further comprising:
  repeatedly generating and sending said sound stimuli to said subject at least at a second measurement session subsequently after a first session, at a later occasion; and
  determining said subject's brainstem response state development by comparing a current lateral brainstem response state to said baseline of said subject, wherein said baseline is established based on the lateral brainstem response state baseline of said subject over the first period of time.

21. The method according to claim 20, further comprising determining a long-term treatment effect or influence of a psychotropic compound or substance or foodstuff or a placebo on said subject's brainstem response state development.

22. A device adapted for quantitatively determining an active psychotropic compound, substance or foodstuff through brain pattern analysis by detecting lateral brainstem response states of a subject over a period of time as a function of a population of neurons' evoked response pattern to sound stimuli, comprising:
  a sound stimuli generating apparatus operative to repeatedly send, over a period of time, identical sound stimuli to said subject to evoke response patterns from a population of neurons in the brainstem, wherein each of said sound stimuli comprises a first train of unmodified sound pulses and at least one second consecutive train of modified sound pulses;
  a detector operative to detect a brainstem response signal related to said response patterns, wherein a first brainstem response signal is caused by said first train of sound pulses and at least one subsequent brainstem response signal is caused by said second consecutive train of modified sound pulses;
  a memory operative to store information based on said brainstem response signals;
  and a computer operative to repeatedly, over said period of time, determine said lateral brainstem response states for each of said sound stimuli, wherein said lateral brainstem response states are relative values based on comparisons between said first brainstem response signal and said at least one subsequent brainstem response signal of said sound stimuli;

wherein said computer is adapted to generate a brainstem response profile of a subject based on said lateral brainstem response states of said subject; and, wherein said computer is adapted to make a comparison between said brainstem response profile and a database comprising information from a population of profiles obtained from a group of subjects being under an influence of a psychotropic compound, substance or foodstuff, and to determine an overlap such that the active psychotropic compound, substance or foodstuff is quantitatively determined.

23. A method for quantitatively determining an active psychotropic compound, substance or foodstuff through brain pattern analysis by detecting lateral brainstem response states of a subject over a period of time as a function evoked response patterns of a population of neurons in the brainstem to sound stimuli, said method comprising:

operating an apparatus for generation of stimuli for repeatedly presenting said subject with an identical sound stimulus, over said period of time, evoking said neurons' response patterns, wherein said sound stimulus comprises a first train of unmodified sound pulses and at least a second consecutive train of modified sounds pulses, wherein said second train of sound pulses comprising at least one modified sound pulse of said first train of sound pulses;

evoking a first brainstem response signal by said first train of unmodified sound pulses and evoking a second brainstem response signal by said second train of modified sound pulses;

operating a detector with an organ for registration of electrophysiological brain activity for detecting said first and second brainstem response signals related to said neurons response patterns;

operating a computer for determining said lateral brainstem response states as relative values repeatedly, over said period of time, based on a comparison between said first and second brainstem response signals of each of said sound stimulus;

generating a brainstem response profile of a subject based on said lateral brainstem response state of said subject; and, making a comparison between said brainstem response profile and a database comprising information from a population of profiles obtained from a group of subjects being under an influence of a psychotropic compound, substance or foodstuff, and determining an overlap such that the active psychotropic compound, substance or foodstuff is quantitatively determined.

* * * * *